US007034046B2

(12) United States Patent
Bauer et al.

(10) Patent No.: US 7,034,046 B2
(45) Date of Patent: Apr. 25, 2006

(54) NR1H4 NUCLEAR RECEPTOR BINDING COMPOUNDS

(75) Inventors: Ulrike Bauer, Sandhausen (DE); Zach Cheruvallath, San Diego, CA (US); Ulrich Deuschle, Bammental (DE); Elena Dneprovskaia, San Diego, CA (US); Tim Gahman, Encinitas, CA (US); Kristina Giegrich, Lampertheim (DE); Ronnie Hanecak, San Clemente, CA (US); Normand Hébert, Cardiff, CA (US); John Kiely, San Diego, CA (US); Ingo Kober, Gaiberg (DE); Manfred Kögl, Eppelheim (DE); Harald Kranz, Leimen (DE); Claus Kremoser, Heidelberg (DE); Matthew Lee, Solana Beach, CA (US); Kerstin Otte, Heidelberg (DE); Carlton Sage, Cardiff, CA (US); Manish Sud, San Diego, CA (US)

(73) Assignee: Phenex Pharmaceuticals AG, (DE)

( * ) Notice: Subject to any disclaimer, the term of this patent is extended or adjusted under 35 U.S.C. 154(b) by 0 days.

(21) Appl. No.: 10/185,721

(22) Filed: Jul. 1, 2002

(65) Prior Publication Data

US 2003/0187042 A1    Oct. 2, 2003

(30) Foreign Application Priority Data

Aug. 13, 2001  (EP)  ................................. 01119473

(51) Int. Cl.
A61K 31/42 (2006.01)
C07D 261/08 (2006.01)
(52) U.S. Cl. ...................... 514/378; 548/247; 548/248
(58) Field of Classification Search ................ 548/247, 548/248; 514/378
See application file for complete search history.

(56) References Cited

U.S. PATENT DOCUMENTS

| 4,634,783 | A | * | 1/1987 | Fujii et al. ................... 549/475 |
| 5,859,257 | A | * | 1/1999 | Talley .......................... 548/247 |
| 6,005,103 | A | * | 12/1999 | Domagala et al. ............. 544/60 |
| 6,051,574 | A |  | 4/2000 | Anthony |
| 6,201,020 | B1 | * | 3/2001 | Zhang et al. ................ 514/544 |
| 2002/0143020 | A1 | * | 10/2002 | Adams et al. ............ 514/254.1 |

FOREIGN PATENT DOCUMENTS

| DE | 19943636 | A1 | * | 3/2001 |
| EP | 0098713 | A2 | * | 1/1984 |
| EP | 573883 | A1 | * | 12/1993 |
| JP | 11/263775 | A | * | 9/1999 |
| WO | WO-00/08001 | A1 | * | 2/2000 |
| WO | WO-00/37077 | A1 | * | 6/2000 |
| WO | WO-00/64876 | A1 | * | 11/2000 |

OTHER PUBLICATIONS

CA Registry No. 433249-96-8, entry date into Registry file on STN is Jun. 22, 2002.*
CA Registry No. 419538-90-2, entry date into Registry file on STN is May 21, 2002.*
CA Registry No. 381677-00-5, entry date into Registry file on STN is Jan. 10, 2002.*
CA Registry No. 354538-63-9, entry date into Registry file on STN is Sep. 4, 2001.*
CA Registry No. 354538-61-7, entry date into Registry file on STN is Sep. 4, 2001.*
CA Registry No. 348601-30-9, entry date into Registry file on STN is Jul. 26, 2001.*
CA Registry No. 348602-52-8, entry date into Registry file on STN is Jul. 26, 2001.*
CA Registry No. 339020-00-7, entry date into Registry file on STN is May 30, 2001.*
CA Registry No. 338978-05-5, entry date into Registry file on STN is May 30, 2001.*
CA Registry No. 324532-75-4, entry date into Registry file on STN is Feb. 27, 2001.*
CA Registry No. 314027-56-0, entry date into Registry file on STN is Jan. 16, 2001.*
CA Registry No. 314027-55-9, entry date into Registry file on STN is Jan. 16, 2001.*
CA Registry No. 314027-54-8, entry date into Registry file on STN is Jan. 16, 2001.*
CA Registry No. 313958-43-9, entry date into Registry file on STN is Jan. 15, 2001.*

(Continued)

*Primary Examiner*—Laura L. Stockton
(74) *Attorney, Agent, or Firm*—Saliwanchik, Lloyd & Saliwanchik

(57) ABSTRACT

The present invention relates to compounds according to the general formula (I) which bind to the nuclear receptor, NR1H4, and act as agonists and antagonists of the NR1H4 receptor. The invention further relates to the treatment of diseases and/or conditions through binding of the nuclear receptor by the compounds.

7 Claims, 7 Drawing Sheets

OTHER PUBLICATIONS

CA Registry No. 313958-42-8, entry date into Registry file on STN is Jan. 15, 2001.*
CA Registry No. 312947-41-4, entry date into Registry file on STN is Jan. 5, 2001.*
CA Registry No. 312947-40-3, entry date into Registry file on STN is Jan. 5, 2001.*
CA Registry No. 312947-39-0, entry date into Registry file on STN is Jan. 5, 2001.*
CA Registry No. 312947-38-9, entry date into Registry file on STN is Jan. 5, 2001.*
CA Registry No. 312947-37-8, entry date into Registry file on STN is Jan. 5, 2001.*
CA Registry No. 312947-36-7, entry date into Registry file on STN is Jan. 5, 2001.*
CA Registry No. 302574-97-6, entry date into Registry file on STN is Nov. 13, 2000.*
CA Registry No. 302573-71-3, entry date into Registry file on STN is Nov. 13, 2000.*
CA Registry No. 261929-20-8, entry date into Registry file on STN is Apr. 14, 2000.*
CA Registry No. 261929-19-5, entry date into Registry file on STN is Apr. 14, 2000.*
CA Registry No. 219865-50-6, entry date into Registry file on STN is Feb. 21, 1999.*
CA Registry No. 219499-05-5, entry date into Registry file on STN is Feb. 7, 1999.*
CA Registry No. 219499-04-4, entry date into Registry file on STN is Feb. 7, 1999.*
CA Registry No. 219499-03-3, entry date into Registry file on STN is Feb. 7, 1999.*
CA Registry No. 219499-02-2, entry date into Registry file on STN is Feb. 7, 1999.*
CA Registry No. 219499-01-1, entry date into Registry file on STN is Feb. 7, 1999.*
CA Registry No. 219140-10-0, entry date into Registry file on STN is Feb. 5, 1999.*
CA Registry No. 218928-39-3, entry date into Registry file on STN is Feb. 3, 1999.*
CA Registry No. 216774-86-6, entry date into Registry file on STN is Jan. 10, 1999.*
Lazzarini et al., CA 96:52213, 1982.*
Pocar et al., CA 94:30610, 1981.*
CA Registry No. 331974-09-5, entry date into Registry file on STN is Apr. 20, 2001.*
CA Registry No. 94084-26-1, entry date into Registry file on STN is Jan. 5, 1985.*
Roussel et al., CA 131:73522, 1999.*
Yakhak Hoechi, "Analgesic, Anti-inflammatory and Antiviral Effects of Melandrin Derivatives", Chemical Abstracts, vol. 121, No. 23, Dec. 5, 1994, (Columbus, OH, USA), p. 39, col. 1, the abstract No. 271343d.
Patrick R. Maloney et al., "Identification of a Chemical Tool for the Orphan Nuclear Receptor FXR", Journal of Medicinal Chemistry, vol. 43, No. 16, Aug. 10, 2000, pp. 2971-2974, XP-002186187.

* cited by examiner

Fig. 2 A

SEQ ID NO. 1

```
MGSKMNLIEH SHLPTTDEFS FSENLFGVLT EQVAGPLGQN LEVEPYSQYS NVQFPQVQPQ    60
ISSSSYYSNL GFYPQQPEEW YSPGIYELRR MPAETLYQGE TEVAEMPVTK KPRMGASAGR   120
IKGDELCVVC GDRASGYHYN ALTCEGCKGF FRRSITKNAV YKCKNGGNCV MDMYMRRKCQ   180
ECRLRKCKEM GMLAECMYTG LLTEIQCKSK RLRKNVKQHA DQTVNEDSEG RDLRQVTSTT   240
KSCREKTELT PDQQTLLHFI MDSYNKQRMP QEITNKILKE EFSAEENFLI LTEMATNHVQ   300
VLVEFTKKLP GFQTLDHEDQ IALLKGSAVE AMFLRSAEIF NKKLPSGHSD LLEERIRNSG   360
ISDEYITPMF SFYKSIGELK MTQEEYALLT AIVILSPDRQ YIKDREAVEK LQEPLLDVLQ   420
KLCKIHQPEN PQHFACLLGR LTELRTFNHH HAEMLMSWRV NDHKFTPLLC EIWDVQ       476
```

FIG 2B

SEQ ID NO. 2

```
atgggatcaa aaatgaatct cattgaacat tcccatttac ctaccacaga tgaattttct    60
ttttctgaaa atttatttgg tgttttaaca gaacaagtgg caggtcctct gggacagaac   120
ctggaagtgg aaccatactc gcaatacagc aatgttcagt ttccccaagt tcaaccacag   180
atttcctcgt catcctatta ttccaacctg ggtttctacc cccagcagcc tgaagagtgg   240
tactctcctg gaatatatga actcaggcgt atgccagctg agactctcta ccagggagaa   300
actgaggtag cagagatgcc tgtaacaaag aagccccgca tgggcgcgtc agcagggagg   360
atcaaagggg atgagctgtg tgttgtttgt ggagacagag cctctggata ccactataat   420
gcactgacct gtgagggtg taaaggtttc ttcaggagaa gcattaccaa aaacgctgtg   480
tacaagtgta aaaacggggg caactgtgtg atggatatgt acatgcgaag aaagtgtcaa   540
gagtgtcgac taaggaaatg caaagagatg ggaatgttgg ctgaatgtat gtatacaggc   600
ttgttaactg aaattcagtg taaatctaag cgactgagaa aaaatgtgaa gcagcatgca   660
gatcagaccg tgaatgaaga cagtgaaggt cgtgacttgc gacaagtgac ctcgacaaca   720
aagtcatgca gggagaaaac tgaactcacc ccagatcaac agactcttct acattttatt   780
atggattcat ataacaaaca gaggatgcct caggaaataa caaataaaat tttaaaagaa   840
gaattcagtg cagaagaaaa ttttctcatt ttgacggaaa tgcaaccaa tcatgtacag    900
gttcttgtag aattcacaaa aaagctacca ggatttcaga ctttggacca tgaagaccag   960
attgctttgc tgaaagggtc tgcggttgaa gctatgttcc ttcgttcagc tgagattttc  1020
aataagaaac ttccgtctgg gcattctgac ctattggaag aaagaattcg aaatagtggt  1080
atctctgatg aatatataac acctatgttt agttttttata aaagtattgg ggaactgaaa  1140
atgactcaag aggagtatgc tctgcttaca gcaattgtta tcctgtctcc agatagacaa  1200
tacataaagg atagagaggc agtagagaag cttcaggagc cacttcttga tgtgctacaa  1260
aagttgtgta agattcacca gcctgaaaat cctcaacact tgcctgtctc ctgggtcgc  1320
ctgactgaat tacggacatt caatcatcac cacgctgaga tgctgatgtc atggagagta  1380
aacgaccaca agtttacccc acttctctgt gaaatctggg acgtgcagtg a           1431
```

FIG. 2C

SEQ ID NO. 3

```
MLVKPLPDSE EEGHDNQEAH QKYETMQCFA VSQPKSIKEE GEDLQSCLIC VARRVPMKER    60
PVLPSSESFT TRQDLQGKIT SLDTSTMRAA MKPGWEDLVR RCIQKFHAQH EGESVSYAKR   120
HHHEVLRQGL AFSQIYRFSL SDGTLVAAQT KSKLIRSQTT NEPQLVISLH MLHREQNVCV   180
MNPDLTGQTM GKPLNPISSN SPAHQALCSG NPGQDMTLSS NINFPINGPK EQMGMPMGRF   240
GGSGGMNHVS GMQATTPQGS NYALKMNSPS QSSPGMNPGQ PTSMLSPRHR MSPGVAGSPR   300
IPPSQFSPAG SLHSPVGVCS STGNSHSYTN SSLNALQALS EGHGVSLGSS LASPDLKMGN   360
LQNSPVNMNP PPLSKMGSLD SKDCFGLYGE PSEGTTGQAE SSCHPGEQKE TNDPNLPPAV   420
SSERADGQSR LHDSKGQTKL LQLLTTKSDQ MEPSPLASSL SDTNKDSTGS LPGSGSTHGT   480
SLKEKHKILH RLLQDSSSPV DLAKLTAEAT GKDLSQESSS TAPGSEVTIK QEPVSPKKKE   540
NALLRYLLDK DDTKDIGLPE ITPKLERLDS KTDPASNTKL IAMKTEKEEM SFEPGDQPGS   600
ELDNLEEILD DLQNSQLPQL FPDTRPGAPA GSVDKQAIIN DLMQLTAENS PVTPVGAQKT   660
ALRISQSTFN NPRPGQLGRL LPNQNLPLDI TLQSPTGAGP FPPIRNSSPY SVIPQPGMMG   720
NQGMIGNQGN LGNSSTGMIG NSASRPTMPS GEWAPQSSAV RVTCAATTSA MNRPVQGGMI   780
RNPAASIPMR PSSQPGQRQT LQSQVMNIGP SELEMNMGGP QYSQQQAPPN QTAPWPESIL   840
PIDQASFASQ NRQPFGSSPD DLLCPHPAAE SPSDEGALLD QLYLALRNFD GLEEIDRALG   900
IPELVSQSQA VDPEQFSSQD SNIMLEQKAP VFPQQYASQA QMAQGSYSPM QDPNFHTMGQ   960
RPSYATLRMQ PRPGLRPTGL VQNQPNQLRL QLQHRLQAQQ NRQPLMNQIS NVSNVNLTLR  1020
PGVPTQAPIN AQMLAQRQRE ILNQHLRQRQ MHQQQQVQQR TLMMRGQGLN MTPSMVAPSG  1080
MPATMSNPRI PQANAQQFPF PPNYGISQQP DPGFTGATTP QSPLMSPRMA HTQSPMMQQS  1140
QANPAYQAPS DINGWAQGNM GGNSMFSQQS PPHFGQQANT SMYSNNMNIN VSMATNTGGM  1200
SSMNQMTGQI SMTSVTSVPT SGLSSMGPEQ VNDPALRGGN LFPNQLPGMD MIKQEGDTTR  1260
KYC                                                               1263
```

FIG. 2D

SEQ ID NO. 4

```
   1 ggcggccgca gcctcggcta cagcttcggc ggcgaaggtc agcgccgacg gcagccggca
  61 cctgacggcg tgaccgaccc gagccgattt ctcttggatt tggctacaca cttatagatc
 121 ttctgcactg tttacaggca cagttgctga tatgtgttca agatgagtgg gatgggagaa
 181 aatacctctg acccctccag ggcagagaca agaaagcgca aggaatgtcc tgaccaactt
 241 ggacccagcc ccaaaaggaa cactgaaaaa cgtaatcgtg aacaggaaaa taaatatata
 301 gaagaacttg cagagttgat ttttgcaaat tttaatgata tagcaacttt taacttcaaa
 361 cctgacaaat gtgcaatctt aaaagaaact gtgaagcaaa ttcgtcagat caaagaacaa
 421 gagaaagcag cagctgccaa catagatgaa gtgcagaagt cagatgtatc ctctacaggg
 481 cagggtgtca tcgacaagga tgcgctgggg cctatgatgc ttgaggccct tgatgggttc
 541 ttctttgtag tgaacctgga aggcaacgtt gtgtttgtgt cagagaatgt gacacagtat
 601 ctaaggtata accaagaaga gctgatgaac aaaagtgtat atagcatctt gcatgttggg
 661 gaccacacgg aatttgtcaa aaacctgctg ccaaagtcta taggtaaatg ggggatcttg
 721 gtctggcgaa cctccgaggc ggaacagcca taccttcaat tgtcggatgc tggtaaaacc
 781 tttacctgat tcagaagagg agggtcatga taaccaggaa gctcatcaga aatatgaaac
 841 tatgcagtgc ttcgctgtct ctcaaccaaa gtccatcaaa gaagaaggag aagatttgca
 901 gtcctgcttg atttgcgtgg caagaagagt tcccatgaag gaaagaccag ttcttccctc
 961 atcagaaagt tttactactc gccaggatct ccaaggcaag atcacgtctc tggataccag
1021 caccatgaga gcagccatga accaggctg ggaggacctg gtaagaaggt gtattcagaa
1081 gttccatgcg cagcatgaag gagaatctgt gtcctatgct aagaggcatc atcatgaagt
1141 actgagacaa ggattggcat tcagtcaaat ctatcgtttt tccttgtctg atggcactct
1201 tgttgctgca caaacgaaga gcaaactcat ccgttctcag actactaatg aacctcaact
1261 tgtaatatct ttacatatgc ttcacagaga gcagaatgtg tgtgtgatga tccggatct
1321 gactggacaa acgatgggga agccactgaa tccaattagc tctaacagcc ctgcccatca
1381 ggccctgtgc agtgggaacc caggtcagga catgaccctc agtagcaata taaatttttcc
1441 cataaatggc ccaaaggaac aaatgggcat gcccatgggc aggtttggtg gttctggggg
1501 aatgaaccat gtgtcaggca tgcaagcaac cactcctcag ggtagtaact atgcactcaa
1561 aatgaacagc ccctcacaaa gcagccctgg catgaatcca ggacagccca cctccatgct
1621 ttcaccaagg catcgcatga gccctggagt ggctggcagc cctcgaatcc cacccagtca
1681 gttttcccct gcaggaagct tgcattcccc tgtgggagtt tgcagcagca caggaaatag
1741 ccatagttat accaacagct ccctcaatgc acttcaggcc ctcagcgagg ggcacggggt
1801 ctcattaggg tcatcgttgg cttcaccaga cctaaaaatg gcaatttgc aaaactcccc
1861 agttaatatg aatcctcccc cactcagcaa gatgggaagc ttggactcaa aagactgttt
1921 tggactatat ggggagccct ctgaaggtac aactggacaa cagagagca gctgccatcc
1981 tggagagcaa aaggaaacaa atgacccaa cctgcccccg gccgtgagca gtgagagagc
2041 tgacgggcag agcagactgc atgacagcaa agggcagacc aaactcctgc agctgctgac
2101 caccaaatct gatcagatgg agccctcgcc cttagccagc tctttgtcgg atacaaacaa
2161 agactccaca ggtagcttgc ctggttctgg gtctacacat ggaacctcgc tcaaggagaa
2221 gcataaaatt ttgcacagac tcttgcagga cagcagttcc cctgtggact tggccaagtt
2281 aacagcagaa gccacaggca agacctgag ccagagtcc agcagcacag ctcctggatc
2341 agaagtgact attaaacaag agccggtgag ccccaagaag aaagagaatg cactacttcg
2401 ctatttgcta gataaagatg atactaaaga tattggttta ccagaaataa ccccaaact
2461 tgagagactg gacagtaaga cagatcctgc cagtaacaca aaattaatag caatgaaaac
2521 tgagaaggag gagatgagct ttgagcctgg tgaccagcct ggcagtgagc tggacaactt
2581 ggaggagatt ttggatgatt tgcagaatag tcaattacca cagctttttcc cagacacgag
2641 gccaggcgcc cctgctggat cagttgacaa gcaagccatc atcaatgacc tcatgcaact
2701 cacagctgaa aacagccctg tcacacctgt ggagcccag aaaacagcac tgcgaatttc
2761 acagagcact tttaataacc cacgaccagg gcaactgggc aggttattgc caaaccagaa
2821 tttaccactt gacatcacat tgcaaagccc aactggtgct ggaccttcc caccaatcag
2881 aaacagtagt ccctactcag tgatacctca gccaggaatg atgggtaatc aagggatgat
2941 aggaaaccaa ggaaatttag ggaacagtag cacaggaatg attggtaaca gtgcttctcg
3001 gcctactatg ccatctgacc aatgggcacc gcagagttcg gctgtgagag tcacctgtgc
3061 tgctaccacc agtgccatga accggccagt ccaaggaggt atgattcgga acccagcagc
3121 cagcatcccc atgaggccca gcagccagcc tggccaaaga cagacgcttc agtctcaggt
3181 catgaatata gggccatctg aattagagat gaacatgggg ggacctcagt atagccaaca
3241 acaagctcct ccaaatcaga ctgccccatg gcctgaaagc atcctgccta tagaccaggc
3301 gtcttttgcc agccaaaaca ggcagccatt tggcagttct ccagatgact tgctatgtcc
3361 acatctgca gctgagtctc cgagtgatga ggaagctctc ctggaccagc tgtatctggc
3421 cttgcggaat tttgatggcc tggaggagat tgatagagcc ttaggaatac ccgaactggt
3481 cagccagagc caagcagtag atccagaaca gttctcaagt caggattcca acatcatgct
3541 ggagcagaag gcgcccgttt cccacagca gtatgcatct caggcacaaa tggcccaggg
3601 tagctattct cccatgcaag atccaaactt tcacaccatg ggacagcggc ctagttatgc
3661 cacactccgt atgcagccca gaccgggcct caggcccacg ggcctagtgc agaaccagcc
3721 aaatcaacta agacttcaac ttcagcatcg cctccaagca cagcagaatc gccagccact
```

```
3781 tatgaatcaa atcagcaatg tttccaatgt gaacttgact ctgaggcctg gagtaccaac
3841 acaggcacct attaatgcac agatgctggc ccagagacag agggaaatcc tgaaccagca
3901 tcttcgacag agacaaatgc atcagcaaca gcaagttcag caacgaactt tgatgatgag
3961 aggacaaggg ttgaatatga caccaagcat ggtggctcct agtggtatgc cagcaactat
4021 gagcaaccct cggattcccc aggcaaatgc acagcagttt ccatttcctc caaactacgg
4081 aataagtcag caacctgatc caggctttac tgggctacg actccccaga gcccacttat
4141 gtcacccga atggcacata cacagagtcc catgatgcaa cagtctcagg ccaacccagc
4201 ctatcaggcc ccctccgaca taaatggatg ggcgcagcg aacatgggcg gaaacagcat 4261 gttttccag cagtccccac cacacttggg gcagcaagca aacaccagca tgtacagtaa
4321 caacatgaac atcaatgtgt ccatggcgac caacacaggt ggcatgagca gcatgaacca
4381 gatgacagga cagatcagca tgacctcagt gacctccgtg cctacgtcag ggctgtcctc
4441 catgggtccc gagcaggtta atgatcctgc tctgagggga ggcaacctgt tcccaaacca
4501 gctgcctgga atggatatga ttaagcagga gggagacaca acacggaaat attgctgaca
4561 ctgctgaagc cagttgcttc ttcagctgac cgggctcact tgctcaaaac acttccagtc
4621 tggagagctg tgtctatttg tttcaaccca actgacctgc cagccggttc tgctagagca
4681 gacaggcctg gccctggttc ccagggtggc gtccactcgg ctgtggcagg aggagctgcc
4741 tcttctcttg acagtctgaa gctcgcatcc agacagtcgc tcagtctgtt cactgcattc
4801 acctagtgc aacttagatc tctcctgcaa aagtaaatgt tgacaggcaa atttcatacc
4861 catgtcagat tgaatgtatt taaatgtatg tatttaagga gaaccatgct cttgttctgt
4921 tcctgttcgg ttccagacac tgtttcttg ctttgtttt cctggctaac agtctagtgc
4981 aaaagattaa gattttatct ggggaaga aagaattt taaaaatt aaactaaga
5041 tgttttaagc taaagcctga atttgggatg gaagcaggac agacaccgtg gacagcgctg
5101 tattacaga cacaccagt gcgtgaagac caacaagtc acagtcgtat ctctagaaag
5161 ctctaaagac catgttggaa agagtctcca gttactgaac agatgaaag cagcctgtga
5221 gagggctgtt aacattagca aatatttttt cctgttttt tgtttgttaa aaccaaactg
5281 gttcacctga atcatgaatt gagaagaaat aattctcatt tctaattaa gtccctttta
5341 gtttgatcag acagcttgaa tcagcatctc ttctttcctg tcagcctgac tcttcccttc
5401 ccctctcta ttccccatac tccctatttt cattccttt ttaaaaaata atataagctc
5461 cagaaccag ctaagcctt tattcctta aatgttttgc cagccactta ccaattgcta
5521 agtattgaat ttcagaaaaa aaaatgcat ttactggcaa ggagaagagc aaagttaagg
5581 cttgatacca atcgagctaa ggatacctgc ttggaagca tgtttattct gttcccagc
5641 aactctggcc tccaaatgg gagaaacgc cagtgtgttt agattgatag cagatatcac
5701 gacagattta acctctgcca tgtcttttt atttgttt ttagcagtgc tgactaagcc
5761 gaagtttgt aagtacata aaatccaatt tatatgtaaa caagcaataa tttaagttga
5821 gaacttatgt gttttaattg tataatttt gtgaggtata catattgtgg aattgactca
5881 aaaatgaggt acttcagtat taattagat atctcatag caatgtctcc taaaggtgtt
5941 ttgtaaagga tatcaatgcc ttgattagac ctaattgta gacttaagac tttttatttt
6001 ctaaaccttg tgattctgct tataagtcat ttatctaatc tatatgatat gcagccgctg
6061 caggaaccaa ttctgactt ttatatgttt atatccttc ttaatgaacc ttagaaagac
6121 tacatgttac taagcaggcc acttttatgg ttgttttt
```

NR1H4 NUCLEAR RECEPTOR BINDING COMPOUNDS

CROSS-REFERENCE TO A RELATED APPLICATION

This application claims priority to European patent application 01119473.5, filed Aug. 13, 2001.

FIELD OF THE INVENTION

This invention relates to compounds that bind to the nuclear receptor, NR1H4, and methods of using such compounds to modulate gene expression.

BACKGROUND OF THE INVENTION

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often simple molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known (Escriva, H. et al., Ligand binding was acquired during evolution of nuclear receptors, PNAS, 94, 6803–6808, 1997). Orphan receptors may be indicative of unknown signaling pathways in the cell or may be nuclear receptors that function without ligand activation. The activation of transcription by some of these orphan receptors may occur in the absence of an exogenous ligand and/or through signal transduction pathways originating from the cell surface (Mangelsdorf, D. J. et al., The nuclear receptor superfamily: the second decade, Cell 83, 835–839, 1995).

In general, three functional domains have been defined in NRs. An amino terminal domain is believed to have some regulatory function. A DNA-binding domain hereinafter referred to as "DBD" usually comprises two zinc finger elements and recognizes a specific hormone responsive element (hereinafter referred to as "HRE") within the promoters of responsive genes. Specific amino acid residues in the "DBD" have been shown to confer DNA sequence binding specificity (Schena, M. & Yamamoto, K. R., Mammalian Glucocorticoid Receptor Derivatives Enhance Transcription in Yeast, Science, 241:965–967, 1988). A Ligand-binding-domain (hereinafter referred to as "LBD") is at the carboxy-terminal region of known NRs. In the absence of hormone, the LBD appears to interfere with the interaction of the DBD with its HRE. Hormone binding seems to result in a conformational change in the NR and thus opens this interference (Brzozowski et al., Molecular basis of agonism and antagonism in the oestogen receptor, Nature, 389, 753–758, 1997; Wagner et al., A structural role for hormone in the thyroid hormone receptor, Nature, 378, 690–697. 1995). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (Heery et al., A signature motif in transcriptional coactivators mediates binding to nuclear receptors, Nature, 387, 733–736; Heinzel et al., A complex containing N-CoR, mSin3 and histone deacetylase mediates transcriptional repression, Nature 387, 43–47, 1997). Furthermore, the physical interaction with negative receptor-interacting proteins or corepressors has been demonstrated (Xu et al., Coactivator and Corepressor complexes in nuclear receptor function, Curr Opin Genet Dev, 9 (2), 140–147, 1999).

Nuclear receptor modulators like steroid hormones affect the growth and function of specific cells by binding to intracellular receptors and forming nuclear receptor-ligand complexes. Nuclear receptor-hormone complexes then interact with a hormone response element (HRE) in the control region of specific genes and alter specific gene expression.

The Farnesoid X Receptor alpha (hereinafter referred to as "FXR"; also often referred to as the nuclear receptor, NR1H4, when referring to the human receptor) is a prototypical type 2 nuclear receptor which activates genes upon binding to promoter region of target genes in a heterodimeric fashion with Retinoid X Receptor (hereinafter RXR, Forman et al., Cell, 81, 687–93, 1995). The relevant physiological ligands of NR1H4 seem to be bile acids (Makishima et al., Science, 284, 1362–65, 1999; Parks et al., Science, 284, 1365–68, 1999). The most potent is chenodeoxycholic acid, which regulates the expression of several genes that participate in bile acid homeostasis. Farnesoid, originally described to activate the rat ortholog at high concentration does not activate the human or mouse receptor. FXR is expressed in the liver, small intestine, colon, ovary, adrenal gland and kidney, and is involved in intracrine signaling.

FXR is proposed to be a nuclear bile acid sensor. As a result, it modulates both, the synthetic output of bile acids in the liver and their recycling in the intestine (by regulating bile acid binding proteins). Upon activation (e.g. binding of chenodeoxycholic acid), it influences the conversion of dietary cholesterol into bile acids by inhibiting the transcription of key genes which are involved in bile acid synthesis such as CYP7A1. This seems to be a major mechanism of feedback regulation onto bile acid synthesis.

The synthetic compounds, 1,1-bisphosphonate esters, appear to display a number of similar activities to the two identified prototypes of natural FXR agonists, farnesol, and chenodeoxycholic acid. Like farnesol, the 1,1-bisphosphonate esters increase the rate of 3-Hydroxy-3-methylglutaryl-CoA (HMG-CoA) reductase degradation and like bile acids they induce the expression of the intestinal bile acid binding protein (hereinafter referred to as "I-BABP") and repress the cholesterol 7 α-hydroxylase gene. Certain 1,1-bisphos-phonate esters also bind to FXR (Niesor et al., Curr Pharm Des, 7(4):231–59, 2001). That means that activation of FXR could lead to opposing effects, i.e., lowering the rate of cholesterol synthesis by increasing degradation of HMG-CoA reductase and increasing the cholesterol pool by inhibition of cholesterol degradation into bile acids. The FXR agonist, chenodeoxycholic acid, does not change cholesterol and lipoprotein levels significantly in patients, although a repression of bile acid synthesis as well as a decreased HMG-CoA Reductase activity was observed (Einarsson et al., Hepatology, 33(5), 1189–93, 2001) confirming that cellular cholesterol synthesis and degradation are controlled by numerous regulatory loops including the coordinate regulation of HMGCoA reductase and cholesterol 7α-hydroxylase and that compounds modulating FXR activity might have different effects on blood lipid parameters.

In the course of functional analysis of certain 1,1-bisphosphonate esters, it was shown that these compounds which are known to bind to FXR also induce apoptosis in a variety of cell types, similar to the isporenoids farnesol and geranylgeraniol which are also known as weak FXR binders (Flach et al., Biochem Biophys Res Com, 270, 240–46, 2000).

To date only very few compounds have been described which bind the NR1H4 receptor and thus show utility for treating diseases or conditions which are due to or influenced by said nuclear receptor (Maloney at al., J Med Chem, 10; 43(16): 2971–2974, 2000).

It was thus an object of the present invention to provide for a novel NR1H4 binding compound. It was also an object of the present invention to provide for compounds which by means of binding the NR1H4 receptor act as agonist or antagonist of said receptor and thus show utility for treating diseases or conditions which are due to or influenced by said nuclear receptor.

It was further an object of the invention to provide for compounds that may be used for the treatment of cholesterol-associated conditions or diseases. In a preferred embodiment of the invention it was an object of the invention to provide for cholesterol lowering or cholestatic compounds. It was also an object of the invention to provide for compounds that may be used for antitumor medicaments.

SUMMARY OF THE INVENTION

The present invention provides, inter alia, novel NR1H4 nuclear receptor protein binding compounds according to the general formula (1) shown below. The compounds are also binders of mammalian homologues of the receptor. Further the object of the invention was solved by providing for amongst the NR1H4 nuclear receptor protein binding compounds according to the general formula (I) below such compounds which act as agonists and such compounds which act as antagonists of the human FXR receptor or a mammalian homologue thereof.

The invention provides for FXR agonists that may be used for the treatment of cholesterol-associated conditions or diseases. In a preferred embodiment of the invention, cholesterol lowering or cholestatic compounds are disclosed. The compounds according to the invention may be used for manufacture of antitumor medicaments and/or for the treatment of diseases such as cancer.

The foregoing merely summarizes certain aspects of the present invention and is not intended, nor should it be construed, to limit the invention in any manner. All patents and other publications recited herein are hereby incorporated by reference in their entirety.

BRIEF DESCRIPTION OF THE DRAWINGS

FIG. 2A is the amino acid sequence of the FXR protein, a portion of which was used for cloning as described in the examples (SEQ ID NO. 1). FIG. 2B shows the nucleotide sequence (SEQ ID NO. 2) of FXR mRNA. FIG. 2C is the amino acid sequence of TIF2 (ACC. NO: XM_011633 REFSEQ DB)(SEQ ID NO.3) and FIG. 2D shows the nucleotide sequence of TIF2 mRNA (SEQ ID NO. 4).

DETAILED DESCRIPTION OF THE INVENTION

Figure 1:
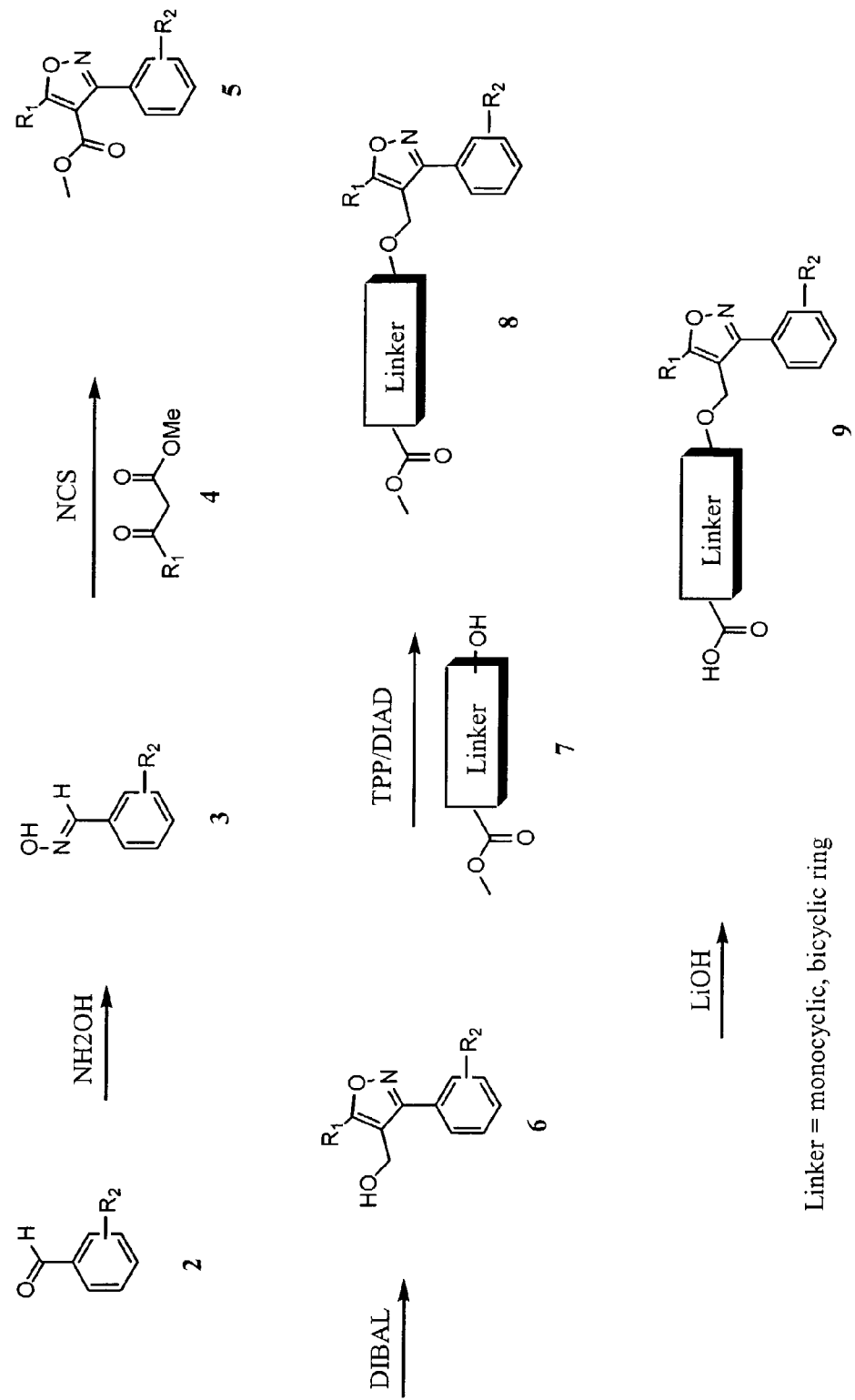
FIG. 1 shows the synthesis of the compounds according to the invention and as described in Example 2.

The invention provides for a compound including resolved diastereoisomers and enantiomers and tautomers, pharmaceutical acceptable salts or solvates thereof (hereinafter also referred to as the "compounds according to the invention"), having the following formula (I):

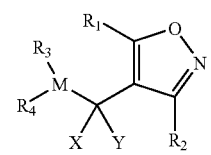

wherein, $R_1$ is hydrogen, $C_1$ to $C_8$ alkyl, $C_1$ to $C_8$ substituted alkyl, phenyl, substituted phenyl, heteroaryl, substituted heteroaryl, heterocycle, substituted heterocycle, naphthyl or substituted naphthyl;

$R_2$ is hydrogen $C_1$ to $C_8$ alkyl, $C_1$ to $C_8$ substituted alkyl, phenyl, substituted phenyl, heteroaryl, substituted heteroaryl, heterocycle, substituted heterocycle, naphthyl or substituted naphthyl;

$R_3$ is absent or if present selected from hydrogen, $C_1$ to $C_8$ alkyl, $C_1$ to $C_8$ substituted alkyl, $C_7$ to $C_{12}$ alkylphenyl or $C_7$ to $C_{12}$ substituted phenylalkyl, phenyl, $C_5$ to $C_6$ heteroaryl, $C_5$ to $C_6$ substituted heteroaryl, substituted phenyl, biphenyl, substituted biphenyl, biphenyl ether, substituted biphenyl ether, biphenyl amine, substituted biphenyl amine, naphthyl and substituted naphthyl; and $R_4$ is absent, or if present, selected from hydrogen, $C_1$ to $C_8$ alkyl, $C_1$ to $C_8$ substituted alkyl, $C_7$ to $C_{12}$ alkylphenyl or $C_7$ to $C_{12}$ substituted phenylalkyl, phenyl, substituted phenyl, $C_5$ to $C_6$ heteroaryl, $C_5$ to $C_6$ substituted heteroaryl, biphenyl, substituted biphenyl, biphenyl ether, substituted biphenyl ether, biphenyl amine, substituted biphenyl amine, naphthyl and substituted naphthyl;

M is O or N or S, however, when M is O or S, one of $R_3$ or $R_4$ must be absent; and X and Y are both hydrogen or both methyl or together represent a carbonyl group;

$R_3$ and $R_4$ may be taken together with nitrogen to form a heterocycle or substituted heterocycle or a heteroaryl or substituted heteroaryl ring.

In one embodiment of the present invention $R_1$ and $R_2$ in formula (I) as shown above are independently selected from the group consisting of $R_1$ is hydrogen, $C_1$ to $C_8$ alkyl, $C_1$ to $C_8$ substituted alkyl; $R_2$ is phenyl, substituted phenyl, heteroaryl, substituted heteroaryl, heterocycle, and substituted heterocycle; $R_3$ is absent, or if present, is select from the group consisting of hydrogen, $C_1$ to $C_8$ alkyl, $C_1$ to $C_8$ substituted alkyl, $C_7$ to $C_{12}$ alkylphenyl or $C_7$ to $C_{12}$ substituted phenylalkyl, phenyl, substituted phenyl, $C_5$ to $C_6$ heteroaryl, $C_5$ to $C_6$ substituted heteroaryl, naphthyl and substituted naphthyl; $R_4$ is absent, or if present, is select from the group consisting of hydrogen, $C_1$ to $C_8$ alkyl, $C_1$ to $C_8$ substituted alkyl, $C_7$ to $C_{12}$ alkylphenyl or $C_7$ to $C_{12}$ substituted phenylalkyl, phenyl, substituted phenyl, $C_5$ to $C_6$ heteroaryl, $C_5$ to $C_6$ substituted heteroaryl, naphthyl and substituted naphthyl; M is O or N or S, however, if M is O or S, one of $R_3$ or $R_4$ must be absent; X and Y are both hydrogen, or both methyl, or together represent a carbonyl group.

In a more preferred embodiment of the present invention $R_1$ is hydrogen, $C_1$ to $C_8$ alkyl or $C_1$ to $C_8$ substituted alkyl, $R_2$ is phenyl, substituted phenyl, heteroaryl, substituted heteroaryl, heterocycle or substituted heterocycle; $R_3$ is absent, or if present, is hydrogen, $C_1$ to $C_8$ alkyl or $C_1$ to $C_8$ substituted alkyl; $R_4$ is $C_7$ to $C_{12}$ substituted phenylalkyl, substituted phenyl, $C_5$ to $C_6$ substituted heteroaryl or substituted naphthyl; M is O or N or S, however, if M is O or S, one of $R_3$ or $R_4$ must be absent; X and Y are both hydrogen, both methyl, or together represent a carbonyl group.

In a more preferred embodiment of the invention, $R_1$ is hydrogen, $C_1$ to $C_8$ alkyl, $C_1$ to $C_8$ substituted alkyl, alkyl phenyl, substituted phenyl, $C_5$ to $C_6$ heteroaryl, $C_5$ to $C_6$ substituted heteroaryl, naphthyl or substituted naphthyl; $R_2$ is substituted phenyl, $C_5$ to $C_6$ heteroaryl or $C_5$ to $C_6$ substituted heteroaryl; $R_3$ has one of the following structures;

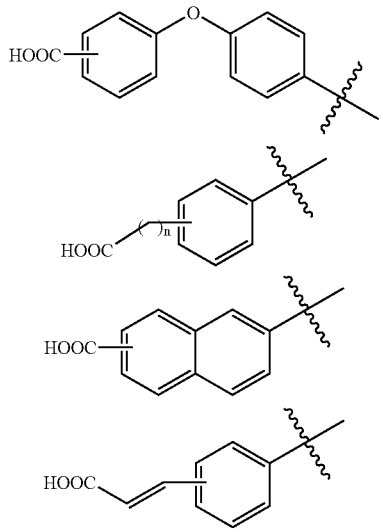

R4 is absent;
M=O,
both X and Y are hydrogen; and
n is an integer from 0 to 8, preferably 1 to 6, and most preferably, 1 to 4.

The symbol in the above formulas and in formula (II) below:

represents a fragment and covalent linkage between the fragment and the aromatic ring.

An even more preferred embodiment of the invention is a compound, or pharmaceutical acceptable salts or solvates thereof, wherein $R_1$ is $C_1$ to $C_8$ alkyl or $C_1$ to $C_8$ substituted alkyl; $R_2$ is substituted phenyl; $R_3$ has the following formula (II):

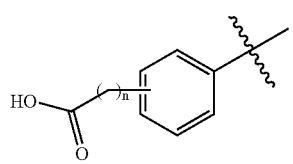

(II)

$R_4$ is absent
M=O,
both X and Y are hydrogen;
and n is an integer from 0 to 8.

A particularly preferred compound which may act as agonist of NR1H4 is shown in formula (II) below. The inventors have been able to demonstrate that the compound according to formula (II) has a low effective concentration at FXR with an $EC_{50}$ of 0.23 µM wherein the $EC_{50}$ reflects the half-maximal effective concentration, and which is higher than the $EC_{50}$ of 0.015 µM for the published FXR agonist GW4064 (B. Goodwin et al., Molecular Cell 6, 517–526, 2000).

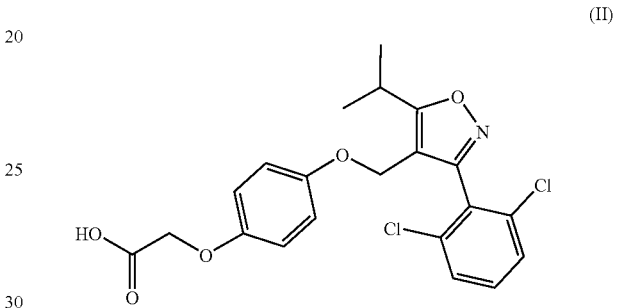

(II)

The inventors have also found the compounds according to formulas III, IV and V below to be active as agonist of the NR1H4 human nuclear receptor (see figures for details).

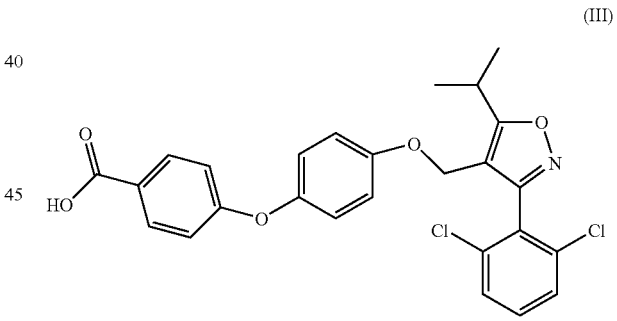

(III)

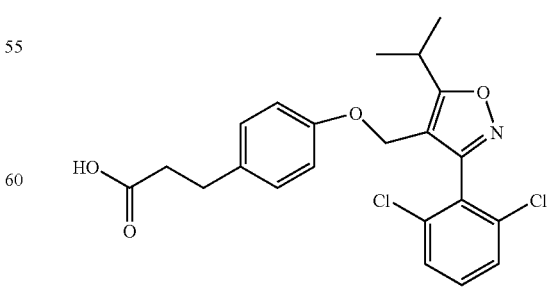

(IV)

-continued (V)

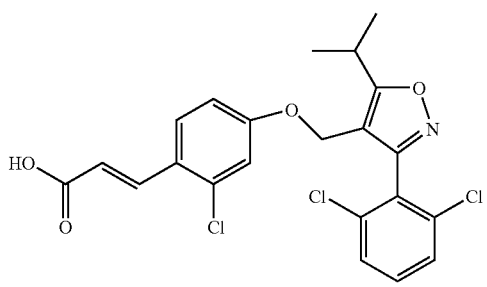

The inventors have identified the compounds as well as the general structure capable of effectively binding FXR.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "halogen" refers to the fluoro, chloro, bromo or iodo atoms. There can be one or more halogen, which are the same or different. Preferred halogens are chloro and fluoro.

The term "$C_1$ to $C_8$ alkyl" denotes such radicals as methyl, ethyl, n-propyl, isopropyl, n-butyl, iso-butyl, sec-butyl, tert-butyl, amyl, tert-amyl, hexyl, n-heptyl, 2-heptyl, 3-heptyl, 4-heptyl, 2-methyl-1-hexyl, 2-methyl-2-hexyl, 2-methyl-3-hexyl, n-octyl and the like.

The term "$C_1$ to $C_8$ substituted alkyl" denotes that the above $C_1$ to $C_8$ alkyl groups are substituted by one or more, and preferably one or two, halogen, hydroxy, protected hydroxy, oxo, protected oxo, $C_3$ to $C_7$ cycloalkyl, phenyl, naphthyl, amino, protected amino, monosubstituted amino, protected monosubstituted amino, disubstituted amino, guanidino, protected guanidino, heterocyclic ring, substituted heterocyclic ring, $C_1$ to $C_8$ alkoxy, $C_1$ to $C_8$ acyl, $C_1$ to $C_8$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, 4-carboxybutyl, 5-carboxypentyl, 6-carboxyhexyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminopropyl, 1-aminoethyl, N-benzoyl-2-aminoethyl, N-acetyl-2-aminoethyl, N-benzoyl-1-aminoethyl, N-acetyl-1-aminoethyl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_8$ alkyl, $C_1$ to $C_8$ substituted alkyl, $C_1$ to $C_8$ alkoxy, $C_1$ to $C_8$ substituted alkoxy, substituted phenoxy, substituted phenyl amine, $C_1$ to $C_8$ acyl, $C_1$ to $C_8$ substituted acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, wherein the phenyl is substituted or unsubstituted, such that, for example, a biphenyl results.

Examples of the term "substituted phenyl" include a mono- or di(halo) phenyl group such as 2, 3 or 4-chlorophenyl, 2,6-difluorophenyl, 2,3-difluorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy) phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl, 4-(4'-carboxy phenoxy)-phenyl, 4-(4'-protected carboxy phenoxy)-phenyl, 4-(3'-carboxy phenoxy)-phenyl, 4-(3'-protected carboxy phenoxy)-phenyl, 4-(4'-carboxy phenyl amino)-phenyl, 4-(4'-protected carboxy phenyl amino)-phenyl, or 4-(3'-carboxy phenyl amino)-phenyl, 4-(3'-protected carboxy phenyl amino)-phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "$C_7$ to $C_{12}$ phenylalkyl" denotes a $C_1$ to $C_6$ alkyl group substituted at any position by a phenyl, substituted phenyl, heteroaryl or substituted heteroaryl. Examples of such a group include benzyl, 2-phenylethyl, 3-phenyl (n-propyl), 4-phenylhexyl, 3-phenyl (n-amyl), 3-phenyl (sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, (monosubstituted) amino, protected (monosubstituted) amino, (disubstituted) amino, guanidino, protected guanidino, heterocyclic ring, substituted heterocyclic ring, $C_1$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substituted acyl, $C_1$ to $C_8$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-($C_1$ to $C_6$dialkyl)carboxamide, cyano, N-($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substituted acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl) carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino, cyclic $C_2$ to $C_8$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-hydroxyphenylmethyl, 3-hydroxyphenylmethyl, 2-methoxyphenylmethyl, 3-methoxyphenylmethyl, 2,6-difluorophenylmethyl, 2,3-difluorophenylmethyl, 2,6-dichlorophenylmethyl, 2,3-dichlorophenylmethyl, 3,5-dichlorophenylmethyl, 2-hydroxyphenylethyl, 3-hydroxyphenylethyl, 2-methoxyphenylethyl, 3-methoxyphenylethyl, 2,6-difluorophenylethyl, 2,3-difluorophenylethyl, 2,6-dichlorophenylethyl, 2,3-dichlorophenylethyl, 3,5-dichlorophenylmethyl 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexamethyleneimino and heptamethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_8$ alkyl, $C_1$ to $C_8$ alkoxy, $C_1$ to $C_8$ substituted alkoxy, $C_1$ to $C_8$ acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino carboxamide, protected carboxamide, N-($C_1$ to $C_{12}$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino, heterocycle or substituted heterocycle groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, thiopheno, oxazolo, isoxazolo, phthalimido, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_8$ alkyl, $C_1$ to $C_8$ alkoxy, $C_1$ to $C_8$ substituted alkoxy, $C_1$ to $C_8$acyl, $C_1$ to $C_8$ substituted acyl, $C_1$ to $C_6$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino groups.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_8$ alkyl, $C_1$ to $C_8$ alkoxy, $C_1$ to $C_8$ acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino.

Examples of the term "substituted naphthyl" includes a mono or di(halo) naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di (hydroxy) naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethyinaphthyl, 1, 2, 3, 4, 5, 6, 7 or 8-(n-propyl)naphthyl and the like; a mono or di(alkoxy)naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy) naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy)naphthyl; a mono-or di(hydroxymethyl)naphthyl or (protected hydroxymethyl)naphthyl such as 1, 2, 3, 4, 5, 6, 7 or 8-(protected hydroxymethyl)naphthyl or 3,4-di(hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2,3, or 4-(aminomethyl)naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

As outlined above $R_3$ and $R_4$ may be taken together with nitrogen to form a heterocycle or substituted heterocycle of the following kind aziridine, azetidine, pyrrolidine, 3-methylpyrrolidine, 3-aminopyrrolidine, 3-hydroxypyrrolidine, pyrazolidine, imidazolidine, piperidine, 2-methylpiperidine, 4-carboxypiperidine, 4-(carboxymethyl) piperidine, piperazine, morpholine, azepine, tetrahydroisoquinoline.

The term "$C_1$ to $C_8$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "$C_1$ to $C_8$ substituted acyl" denotes the acyl group substituted by one or more, and preferably one or two, halogen, hydroxy, protected hydroxy, oxo, protected oxo, cyclohexyl, naphthyl, amino, protected amino, monosubstituted amino, protected monosubstituted amino, disubstituted amino, guanidino, heterocyclic ring, substituted heterocyclic ring, imidazolyl, indolyl, pyrrolidinyl, $C_1$ to $C_8$ alkoxy, $C_1$ to $C_8$ acyl, $C_1$ to $C_8$ acyloxy, nitro, $C_1$ to $C_8$ alkyl ester, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_8$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl and the like.

The term "$C_1$ to $C_8$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_8$ substituted alkoxy" means the alkyl portion of the alkoxy can be substituted in the same manner as in relation to $C_1$ to $C_8$ substituted alkyl.

The term "$C_1$ to $C_8$ substituted aminoacyl" denotes the acyl group substituted by one or more, and preferably one or two, halogen, hydroxy, protected hydroxy, oxo, protected oxo, cyclohexyl, naphthyl, amino, protected amino, mono-substituted amino, protected monosubstituted amino, disubstituted amino, guanidino, heterocyclic ring, substituted heterocyclic ring, imidazolyl, indolyl, pyrrolidinyl, $C_1$ to $C_8$ alkoxy, $C_1$ to $C_8$ acyl, $C_1$ to $C_8$ acyloxy, nitro, $C_1$ to $C_8$ alkyl ester, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, cyano, methylsulfonylamino, thiol, $C_1$ to $C_6$ alkylthio or $C_1$ to $C_6$ alkylsulfonyl groups. The substituted acyl groups may be substituted once or more, and preferably once or twice, with the same or with different substituents.

This invention provides a pharmaceutical composition comprising an effective amount of at least one compound according to the invention. Such compositions can be administered by various routes, for example oral, subcutaneous, via suppositories intramuscular, intravenous or intracerebral. The preferred route of administration would be oral at daily doses of the compound for adult human treatment of about 0.01–5000 mg, preferably about 1–1500 mg per day. The appropriate dose may be administered in a single dose or as divided doses presented at appropriate intervals for example as two, three four or more subdoses per day.

For preparing pharmaceutical compositions containing at least one compound of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component. In tablets, the active compound is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound(s) with encapsulating material as a carrier providing a capsule in which the active component(s) (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

In particular the invention relates to compounds as described above wherein the compounds are capable of binding the NR1H4 receptor protein or a portion thereof as shown in SEQ ID NO. 1 (FIG. 2A) or a mammalian homologue thereof. The compounds can bind to the NR1H4 receptor protein or a portion thereof in a mixture comprising about 10–200 ng of NR1H4 receptor protein or a portion thereof, preferably the ligand binding domain, 20 mM Tris/HCl at pH 7.9; 60 mM KCl; 5 mM $MgCl_2$; 160 ng/μl BSA in a total volume of preferably about 25 μl.

A mammalian receptor protein homologue of the protein according to SEQ ID NO. 1 as used herein is a protein that performs substantially the same function as NR1H4 does in humans and shares at least about 40% sequence identity at the amino acid level, preferably about 50% sequence identity at the amino acid level more preferably about 65% sequence identity at the amino acid level, even more preferably about 75% sequence identity at the amino acid level and most preferably over about 85% sequence identity at the amino acid level.

Table 1 shows the structures of preferred compounds according to the invention. The table further shows their respective $EC_{50}$ values (EC50 AVG) as established according to results of multiple experiments, as well as their respective average efficacy (% activity relative to CDCA control agonist).

TABLE 1

| MOLNAME | MOLECULE STRUCTURE | EC50 AVG | EFFIC AVG |
|---|---|---|---|
| LN0000006772 | | 0.05 | 100 |
| LN0000006767 | | 0.23 | 117 |
| LN0000006765 | | 0.43 | 115 |
| LN0000006734 | | 0.6 | 85 |

TABLE 1-continued
| MOLNAME | MOLECULE STRUCTURE | EC50 AVG | EFFIC AVG |
|---|---|---|---|
| LN0000006764 | 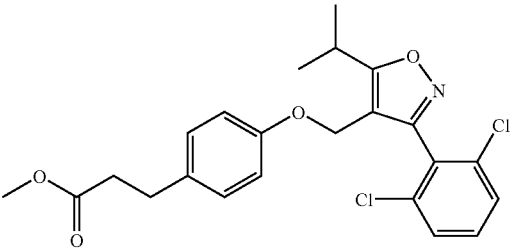 | 0.72 | 108 |
| LN0000000169 | 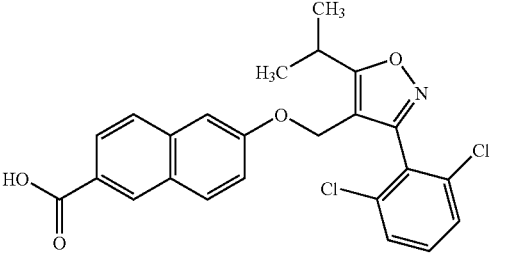 | 2.6 | 134 |
Table 2 shows various known FXR ligands. It is apparent from their structures that the inventors have identified novel compounds that are structurally not related to these known ligands.
TABLE 2
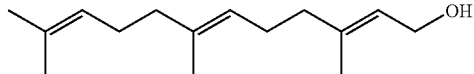
Farnesol
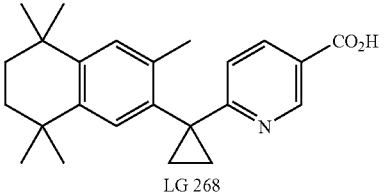
Farnesoic acid
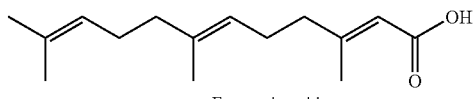
All trans-Retinoic acid
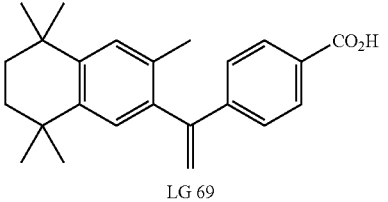
TTNPB
TABLE 2-continued
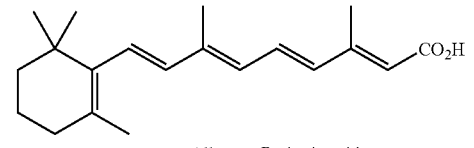
LG 268
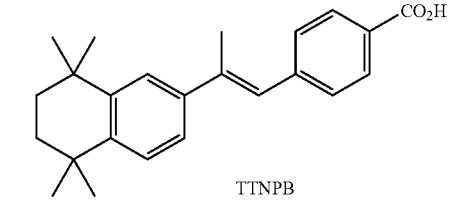
LG 69
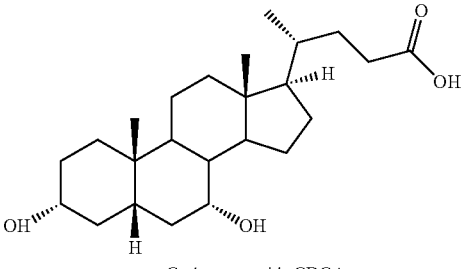
Carboxysteroids CDCA TABLE 2-continued

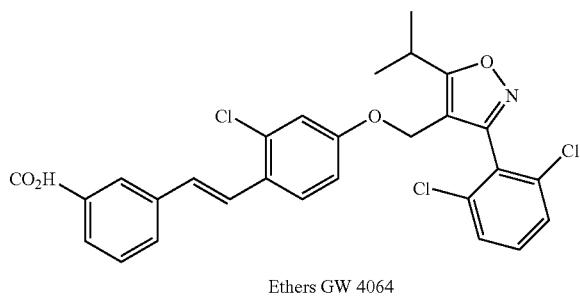

Ethers GW 4064

In another aspect of the invention, there are provided methods for prevention or treatment of a NR1H4 receptor protein- or NR1H4 receptor protein homologue-mediated disease or condition in a mammal comprising administration of a therapeutically effective amount of a compound or combination of compounds according to the invention wherein the prevention or treatment is directly or indirectly accomplished through the binding of the compound(s) according to the invention to the NR1H4 receptor protein or to the NR1H4 receptor protein homologue.

The term mediated herein means that the physiological pathway in which the NR1H4 receptor protein acts is either directly or indirectly involved in the disease or condition to be treated or prevented. In the case where it is indirectly involved it could be that, e.g. modulating the activity of NR1H4 by a compound according to the invention influences a parameter that has a beneficial effect on a disease or a condition. One such example is that modulation of NR1H4 activity leads to decreased levels of serum cholesterol or certain lipoproteins, e.g., LDL or VLDL lipoprotein, or leads to an increase in HDL, for example, which in turn have a beneficial effect on the prevention and treatment of atherosclerosis.

Herein a condition is a physiological or phenotypic state that is desirably altered. One such example would be obesity, which is not necessarily medically harmful, but nonetheless a non-desirable phenotypic condition. In a preferred embodiment of the invention the method for prevention or treatment of a NR1H4 receptor protein mediated disease or condition is applied to a human. This may be male or female.

Pharmaceutical compositions generally are administered in an amount effective for treatment or prophylaxis of a specific condition or conditions. Initial dosing in a human is accompanied by clinical monitoring of symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, doses are from about 100 µg/kg to about 5 mg/kg body weight, daily.

For administration particularly to mammals, and particularly humans, it is expected that the daily dosage level of active agent will be about 0.1 mg/kg to about 10 mg/kg and typically around about 1 mg/kg.

By "therapeutically effective amount" is meant a symptom-alleviating or symptom-reducing amount, a cholesterol-reducing amount, a fatty acid absorption decreasing amount, a protein and/or carbohydrate digestion-blocking amount and/or a de novo cholesterol biosynthesis-blocking amount of a compound according to the invention. Blocking may be partial blocking, i.e., a decrease is observed, or total blockage may occur.

FXR is proposed to be a bile acid sensor. As a result, it modulates both the synthetic output of bile acids in the liver and their recycling in the intestine, by regulating bile acid binding proteins. In one embodiment of the invention, the invention concerns a method for regulating the bile transport system in a mammal. In a human, the method comprises activating the NR1H4 receptor with a therapeutically effective amount of a compound according to the invention.

Likewise the invention concerns a method of treating in a mammal a disease which is affected by cholesterol, triglyceride, or bile acid levels comprising administering to the mammal a therapeutically effective amount of a compound according to the invention.

Accordingly, the compounds according to the invention may also be used as a method of prevention or treatment of mammalian atherosclerosis, gallstone disease, lipid disorders, obesity or cardiovascular disorders such as coronary heart disease or stroke.

The invention further concerns a method of blocking fatty acid absorption in the intestine of a mammal comprising administering to the mammal a therapeutically effective amount of a compound according to the invention. The invention may also be used to treat obesity in humans.

The FXR alpha is a prototypical type 2 nuclear receptor that activates genes upon binding to the promoter region of target genes in a heterodimeric fashion with RXR. The relevant physiological ligands of NR1H4 are bile acids. The present compounds according to the invention have been demonstrated to have a high binding efficacy (binding coefficients measured as IC50 in the range 200 nM to 1000 nM), as well as agonistic and/or antagonistic properties. Consequently, they may be applied to regulate genes that participate in bile acid homeostasis as well as other downstream regulated genes. Examples of such genes include, but are not limited to, lipid absorption, cholesterol biosynthesis, cholesterol transport or binding, bile acid transport or binding, proteolysis, amino acid metabolism, glucose biosynthesis, protein translation, electron transport, and hepatic fatty acid metabolism. FXR often functions in vivo as a heterodimer with the RXR. Published FXR agonists such as the Glaxo SmithKline compound "GW 4064" (See Table 2) are known to influence the regulation of various liver genes. Genes found to be regulated by GW 4064 are genes that down regulate in the liver, genes that up-regulate in the liver and genes that have altered expression in the intestine.

Genes down-regulated in the liver include apolipoprotein B; plasma proteinase inhibitor alpha-1-inhibitor III group 3(m22360); L-glucono-gamma-lactone oxidase (d12754); peroxisomal enoyl-CoA: hydrotase-3-hydroxyacyl-CoA bifunctional enzyme (k03249) liver fatty acid binding protein (L-FABP, m13501), CYP4A2(m57719, and CYP3A23 (x96721); CYP3A1 (x64401); cholesterol-7-alpha-hydroxylase, CYP7A1 (RefSeq NM000780, XM 005022, XM 044651, and XM 044652); and sodium-taurocholate cotransport protein, ntcp (RefSeq NM003049, XM007466). Genes up-regulated in the liver include small heterodimer partner homolog (d86580); bile salt export pump, bsep (RefSeq NM 003742, XM 003644, and XM 033122); phospholipid transfer protein, PLTP (RefSeq NM 006227, XM 009490, XM 029929, and XM 029930); carnitine palmitoyltransferase II, CPTII (RefSeq NM 000098, XM 001758, XM 038866, and XM 038867); phenylethanolamine-N-methyltransferase, PNMT (RefSeq NM 002686, XM 008597, and XM 049837); insulin-induced growth-response protein CL-6

(l13619); elongation factor 2, EF-2 (y07504); mouse cornichon; protein kinase C receptor (u03390); mitochondrial cytochrome c oxidase (m27315); cystathione gamma-lyase (x53460, d17370); cytosolic phosphoenolypyruvate carboxykinase (k03243); histidase (m58308); s-adenosylmethionine synthetase (x60822); lanosterol 14-alpha-demethylase (u17697); G protein-coupled purinoceptor P2U (146865); and hepatic squalene synthetase (m95591). Genes having altered expression in the intestine: include lipase (x61925); pancreatic lipase (d88534); colipase (m58370); pancreatic phospholipase A-2 (d00036); pancreatic amylase (m24962); carboxypeptidase A1 (m23986); carboxypeptidase A2 (m23721); carboxypeptidase B (m23959); pancreatic trypsin I (j00778); pancreatic cationic trypsinogen (m 16624); pancreatic trypsinogen II (v01274); elastase I (v01234, 100112); elastase II (100118, 100124); I-BABP (122788); intestinal fatty acid binding protein (FABP, k01180); hepatic squalenesynthetase (m95591); protein kinase C receptor (u003390); elongation factor 2, EF-2 (y07504); and small heterodimer partner homolog (d86580).

Thus, the invention also concerns a method of modulating a gene whose expression is regulated by the NR1H4 receptor in a mammal comprising administration of a therapeutically effective amount of a compound according to the invention to the mammal.

It is known that the orphan receptor FXR can bind the response element of the shp gene as a heterodimer with RXR (9-cis retinoic acid receptor) and the SHP-protein, in turn, prevents efficient transcription from the cyp7a1 promoter (Lu et al., Mol Cell, 6(3):505–17; Goodwin et al. Mol Cell, 6(3), 717–26, 2000). Another gene that is repressed via SHP upon FXR activation is the sodium/bile acid cotransporter gene, ntcp, a membrane transport protein which is required for the import of conjugated bile acids in the hepatocyte (Denson et al., Gastroenterology; 121(1):218–20, 2001). The gene for the bile salt export pump, a membrane transporter responsible for the secretion of bile acids into the gall is directly activated by FXR (Ananthanarayanan et al., J Biol Chem, 3;276(31):28857–28865, 2001). Consequently, the invention likewise concerns a method for lowering the expression of cholesterol 7-alpha-hydroxylase and NTCP and increasing expression of BSEP in parallel by use of the compounds according to the invention. In one embodiment the invention concerns a method for enhancing the expression of the I-BABP (Grober et al., J Biol Chem, 15;274(42): 29749–54, 1999) and/or the activity of the canicular bile salt excretion pump.

The compounds according to the invention may be used as medicaments, in particular for the prevention or treatment of a NR1H4 receptor protein- or NR1H4 receptor protein homologue-mediated disease or condition in a mammal wherein the prevention or treatment is directly or indirectly accomplished through the binding of the compound or combination of compounds according to the invention to the NR1H4 receptor protein or NR1H4 receptor protein homologue. These pharmaceutical compositions contain about 0.1% to about 99.5% of the compound according to the invention, more particularly about 0.5% to about 90% of the compound according to the invention in combination with a pharmaceutically acceptable carrier.

The invention also concerns the use of a compound or combination of compounds according to the invention for the prevention or treatment of a NR1H4 receptor protein-mediated disease or condition wherein the mammal is a human. The compound(s) may be used for example, for regulating the bile transport system in a mammal, preferentially a human by activating the NR1H4 receptor, or for regulating levels of cholesterol, triglyceride, and/or bile acid in mammals, preferentially humans. The compound(s) may also be used for the treatment of atherosclerosis, gallstone disease, lipid disorders, obesity or a cardiovascular disorder.

The invention further concerns the use of a compound or combination of compounds according to the invention for blocking in a mammal, preferentially a human, fatty acid absorption in the intestine. Further, the inventive compounds may be used alone or in combination, for treating obesity in humans and for modulating a gene whose expression is regulated by the NR1H4 receptor. The invention further concerns the use of a compound or combination of compounds according to the invention for antitumor medicaments. The antitumor effects of such medicaments could be exerted by selective inhibition of cell proliferation and induction of apoptosis of tumor cells in a way similar to described activities for certain bisphosphonates (Alberts D S, et al., Clin Cancer Res May 2001; 7(5):1246–50.

EXAMPLE 1

In Vitro Screening for Compounds which Influence FXR Binding to Coactivators

For screening purposes a fragment of the open reading frame of human FXR alpha (NR1H4—(Acc. No:AF384555)) encoding amino acids 187–472 was amplified by standard RT PCR procedures (see FIGS. 2A and 2B; SEQ ID NO. 1 and 2). Starting material was total RNA derived from human liver. The resulting cDNA obtained after reverse transcription was subsequently cloned using the Gateway™ recombination technology (Invitrogen, USA) into the expression plasmid pDest15 (Invitrogen, USA). This construct was used to express a recombinant GST-FXR fusion protein in *E.coli* (BL21 strain). A pDEST 17 derivative clone harboring an additional sequence encoding amino acids 548–878 of human TIF2 (Acc. No: XM_011633 RefSeq) (see FIGS. 2C and 2D, SEQ ID NO. 3 and 4) was constructed using Gateway™ recombination technology (Invitrogen, USA) in order to obtain a construct which was used to express recombinant His-tagged TIF2 fragment could be expressed in *E. coli*. For *E. coli* expression of both constructs, plasmid DNA was transformed into chemically competent *E. coli* BL21 (Invitrogen, USA) and cells were grown to an OD600 of 0.4–0.7 before expression was induced by addition of 0.5 mM IPTG according instructions of the manufacturer (Invitrogen). After induction for 8 hours at 30° C. cells were harvested by centrifugation for 10 minutes at 5000×g. Fusion proteins were affinity purified using Glutathion sepharose (Pharmacia) or Ni-NTA Agarose (QIAGEN) according to the instructions of the respective manufacturer. Recombinant proteins were dialyzed against 20 mM Tris/HCL pH 7.9; 60 mM KCl; 5 mM $MgCl_2$; 1 mM DTT, 0.2 mM PMSF; and 10% glycerol. The TIF2 fragment was subsequently biotinylated by addition of 40–120 μl of a biotinamidocaproate N-hydroxysuccinimide-ester (Sigma) solution (20 mg/ml in DMSO). Overhead rotating samples were incubated for two hours at room temperature. Unincorporated label was then separated using G25 Gel filtration chromatography (Pharmacia Biotech, Sweden). Protein containing fractions from the column were pooled and tested for activity in the assay as described below.

For screening of compound libraries as provided for by the methods shown below in the examples for substances which influence the FXR/Tif 2 interaction, the Perkin Elmer LANCE technology was applied. This method relies on the binding dependent energy transfer from a donor to an acceptor fluorophore attached to the binding partners of interest. For ease of handling and reduction of background from compound fluorescence LANCE technology makes use of generic fluorophore labels and time resolved detection (for detailed description See Hemmilä I, Blomberg K and Hurskainen P, Time-resolved resonance energy transfer (TR-FRET) principle in LANCE, Abstract of Papers Presented at the 3rd Annual Conference of the Society for Biomolecular Screening, Sep., California (1997)).

For screening, 20–200 ng of biotinylated Tif 2 fragment and 10–200 ng of GST-FXR fragment were combined with 0.5–2 nM LANCE Eu-(W1024) labeled anti-GST antibody (Perkin Elmer) and 0.5–2 µg of Highly fluorescent APC-labeled streptavidin (Perkin Elmer) in the presence of 50 µM of individual compounds to be screened in a total volume of 25 µl of 20 mM Tris/HCl pH 7.9; 60 mM KCl; 5 mM $MgCl_2$; and 160 ng/µl BSA. DMSO content of the samples was kept below 4%. Samples were incubated for a minimum of 60 minutes in the dark at room temperature in FIA-Plates black 384well med. binding (Greiner).

The LANCE signal was detected by a Perkin Elmer VICTOR2V™ Multilabel Counter applying the detection parameters listed in Table 3, below. The results were visualized by plotting the ratio between the emitted light at 665 nm and at 615 nm. For every batch of recombinant proteins amount of proteins and labeling reagents giving the most sensitive detection of hits was determined individually by analysis of dose response curves for chenodeoxycholic acid.

TABLE 3

| | |
|---|---|
| Number of repeats | 1 |
| plate: GREINER FIA-Plate black 384 well med. binding | |
| Measurement height | 3.50 mm |
| Label technology | TR-F Lance |
| Emission filter name | D615 |
| Emission filter slot | A1 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |
| Label technology | TR-F Lance |
| Emission filter name | D665 |
| Emission filter slot | A8 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |

EXAMPLE 2

Experimental Procedure for the Preparation of the Compounds According to the Invention The following steps describe the experimental procedure for the preparation of the compounds according to the invention. The synthesis scheme is shown in FIG. 1.

Step 1: Synthesis of Dicholorobenzaldehyde Oxime (Compound 3).

A solution of 2,6-dichlorobenzaldehyde (compound 2) (0.14 mole) in ethanol (200 mL) was added to a solution of hydroxylamine hydrochloride (0.16 mole) and sodium hydroxide (0.16 mole) in water (100 ml). The resulting mixture was stirred at 90° C. for 24 hours. The volume of the reaction mixture was reduced in vacuo by ~30 mL, which induced a precipitate. The white solids were collected by filtration and washed with water (2×100 mL) to yield (96%) of dicholorobenzaldehyde oxime (compound 3).

Step 2: Synthesis of 3-(2,6-dichlorophenyl)-4-carbomethoxy-5-isopropyl-isoxazole (Compound 5)

N-chlorosuccinimide (0.07 mole) was added at room temperature to a solution of 2,6-dichlorobenzaldehyde oxime (compound 3) (0.07 mole) in DMF (150 mL). The reaction was slightly exothermic and the reaction mixture turned into dark yellow color. The reaction mixture was stirred for an additional one hour, and then the contents were poured into water (200 mL) and extracted with diethyl ether (300 mL). The organic layer was washed with water (3×100 mL) and brine (50 mL), dried ($Na_2SO_4$) and concentrated to obtain 2,6-dicholorophenylhydroximic chloride (94%). A stirred solution of methyl isobutyryl acetate (compound 4) (15.6 mmol) in tetrahydrofuran (15 mL) was treated with a solution of sodium methoxide (31.5 mL, 0.5M in methanol) followed by a solution of 2,6-dicholorophenylhydroximic chloride (15.6 mmol) in tetrahydrofuran (5 mL). After stirring at room temperature for 16 hours the solvent was removed in vacuo. The resulting residue was partitioned with diethyl ether (100 mL) and water (100 mL). The ether layer was washed with brine (50 mL), dried ($Na_2SO_4$), and concentrated to obtain a residue which was purified by flash column chromatography on silica gel using 10% ethyl acetate in hexane as mobile phase to yield 3.1 g(62%) of 3-(2,6-dichlorophenyl)-4-carbomethoxy-5-isopropyl-isoxazole (compound 5).

Step 3: Reduction

A solution of 3-(2,6-dichlorophenyl)-4-carbomethoxy-5-isopropyl-isoxazole (compound 5) (27 mmol) in tetrahydrofuran (60 mL) was cooled to 0° C. under a nitrogen atmosphere. A solution of diisobutylaluminum hydride (38 ml 2.1 eq, 1.5 M in toluene) was added dropwise. The reaction mixture was allowed to warm up to room temperature and was stirred for an additional 16 hours. The reaction mixture was cooled to 0° C. and quenched with methanol (2 mL). When water (20 mL) was added dropwise a gelatinous precipitate was obtained. Sodium hydroxide (30 mL, 2N) was then added and the material was filtered through celite. The filtrate was extracted with ethyl acetate, washed with water and saturated sodium chloride solution, dried ($Na_2SO_4$), and concentrated to obtain the alcohol (compound 6).

Step 4: Mitsunobu Reaction

To a solution of phenol (compound 7) (0.6 mmol), isoxazole (compound 6) (0.6 mmol) and triphenylphosphine (0.6 mmol) in dichloromethane (10 mL), diisopropyl azodicarboxylate((0.6 mmol) was added dropwise. A brief exotherm was observed and the reaction mixture was stirred at room temperature for 4 hours. The reaction mixture was concentrated to a residue and was purified by flash column chromatography using 20% ethyl acetate in hexane as eluant to obtain 8 in 85% yield.

Step 5: Ester Hydrolysis

Lithium hydroxide (0.8 mmol, 1M in water) was added to a solution of ester (compound 8) (0.2 mmol) in THF (5 mL). The reaction mixture was stirred vigorously at room temperature for 24 hours. THF was removed in vacuo and the reaction mixture was extracted with ethyl acetate, dried ($Na_2SO_4$), and concentrated to obtain an oil which was purified by flash column chromatography to form compound 8.

All of the final products were analyzed using an Evaporative Light Scattering Detector (ELSD) detection to determine purity. One skilled in the art will be able to arrive at the compounds claimed herein making use of the above protocol.

A compound according to the invention (experiments shown were done with MOLSTRUCTURE LN 0000006734; see Table 1 for structural formula) can mediate transactivation of FXR-mediated transcription in a HEK293 reporter cell line. Stable HEK293FXR reporter cell lines were generated by stably transfecting with the pTRexDest30 (Invitrogen) derivatives pTRexDest30-hFXR, pTRexDest30-hRXR□ and the pGL2promoter (Promega) derivative, pGL2promoter-FXRRE. The full length human FXR (accession U68233) and the full length human RXRα (accession P19793) were cloned into the pTRexDest30 applying the manufacturer protocols for the Gateway™ system (Invitrogen).

The FXR response elements were cloned (upper case). 5'-cccaGGGTGAaTAACCTcggggctct-gtccctccaatcccaGGGTGAaTAACCTcggg 3' (SEQ ID NO. 5) was obtained from the human IBAB-P promoter (Grober et al 1999, JBC 274, pp. 29749–29754). A stable clone was selected and seeded at a density of $5\times10^4$ cells per well in 48 well plates. Luciferase reporter activity was measured in duplicates from extracts of cells after incubating cells in culture medium (DMEM [Gibco-BRL]+10% FCS [PAA laboratories]) for 16 hours (5% $CO_2$, 37° C.) containing 0.5% DMSO (control) or 0.5% DMSO with increasing concentrations of LN 0000006734.

Figure 3:
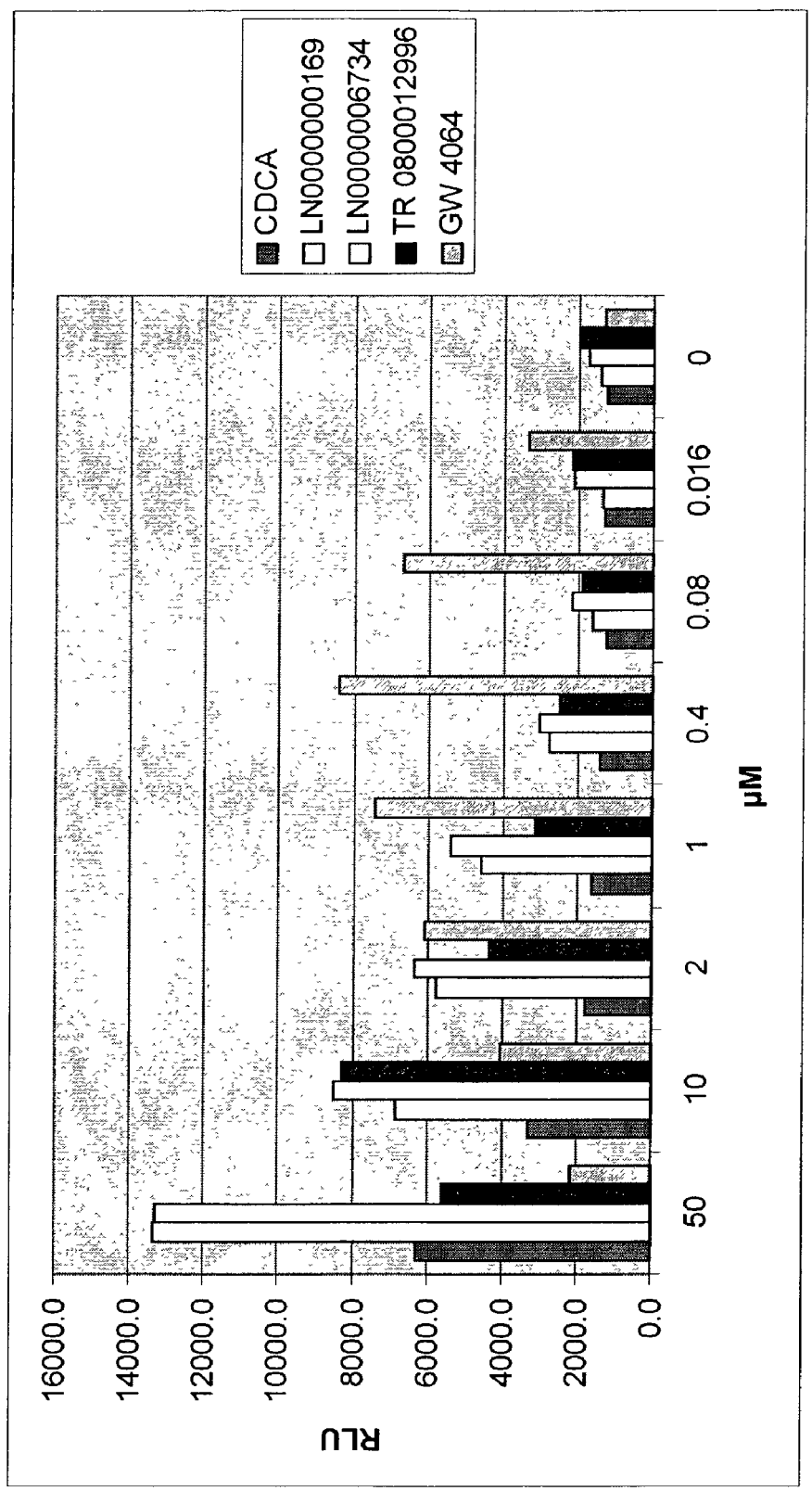
FIG. 3 shows a dose-dependent transactivation (EC50~1 µM) of the reporter gene, luciferase, by FXR.

The data are set forth in Table 4 below. A dose-dependent transactivation (EC50~1 μM) of the reporter gene by FXR was observed and is illustrated in FIG. 3. Variations of duplicate measurements are within 20%.

TABLE 4

| μM | CDCA | LN0000000169 | LN0000006734 | TR 0800012996 | GW 4064 |
|---|---|---|---|---|---|
| 50 | 6310.0 | 13375.7 | 13309.5 | 5626.0 | 2159.3 |
| 10 | 3300.7 | 6829.3 | 8523.5 | 8286.0 | 4030.3 |
| 2 | 1784.0 | 5775.7 | 6330.5 | 4341.0 | 6084.0 |
| 1 | 1597.7 | 4600.0 | 5360.5 | 3118.0 | 7440.7 |
| 0.4 | 1421.8 | 2754.0 | 2991.5 | 2491.0 | 8416.3 |
| 0.08 | 1256.5 | 1630.0 | 2153.0 | 1896.0 | 6704.7 |
| 0.016 | 1294.3 | 1333.0 | 2077.0 | 2132.0 | 3319.0 |
| 0 | 1257.7 | 1396.3 | 1748.8 | 1971.1 | 1274.1 |

All data are measured in triplicates
max standard deviation +/−20%

While the salient features of the invention have been illustrated and described with respect to particular embodiments, it should be readily apparent that modifications can be made within the spirit and scope of the invention, and it is, therefore, not desired to limit the invention to the exact details shown and described.

What is claimed is:

1. A compound or a pharmaceutical acceptable salt or solvate thereof, wherein said compound has the following structure:

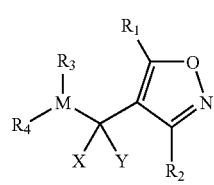

wherein:
  $R_1$ is $C_1$ to $C_8$ alkyl, or $C_1$ to $C_8$ substituted alkyl;
  $R_2$ is phenyl substituted with one or more halogens;
  $R_3$ has one of the following structures:

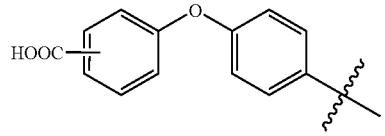

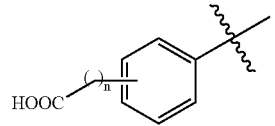

-continued

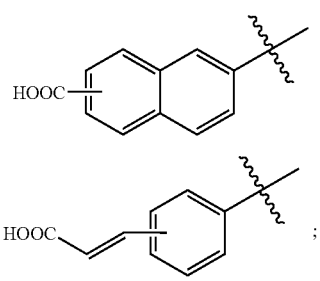

R₄ is absent,
M=O, both X and Y are hydrogen, and n is an integer from 0 to 8.

2. The compound of claim 1, wherein:
R₃ has the following structure:

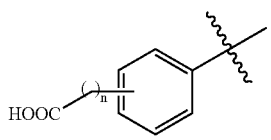

R₄ is absent; M is O; n is an integer from 0 to 8; and X and Y are both hydrogen.

3. The compound according to claim 1, wherein the compound is

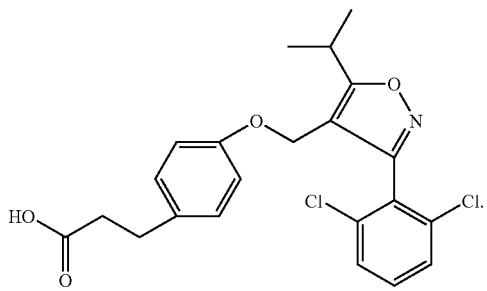

4. The compound according to claim 1, wherein the compound is

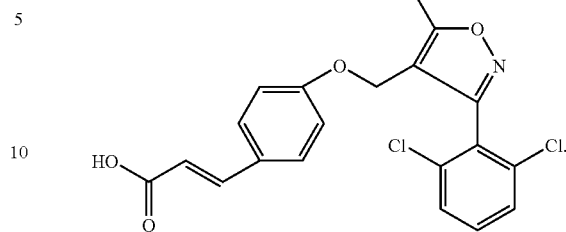

5. The compound according to claim 1, wherein the compound is

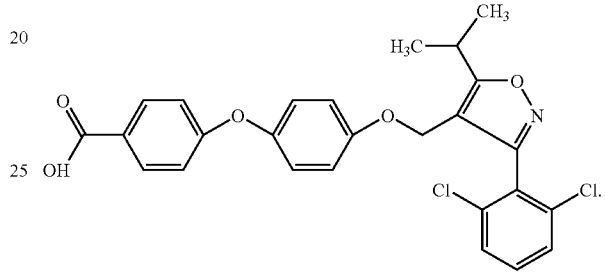

6. The compound according to claim 1, wherein the compound is

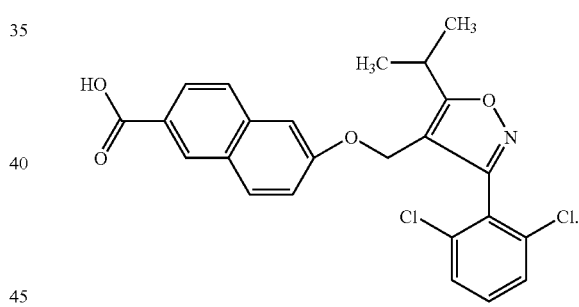

7. A therapeutic composition comprising at least one compound according to claim 1 in admixture with a pharmaceutically acceptable carrier, adjuvant or vehicle.

* * * * *

UNITED STATES PATENT AND TRADEMARK OFFICE
CERTIFICATE OF CORRECTION

| | | |
|---|---|---|
| PATENT NO. | : 7,034,046 B2 | Page 1 of 1 |
| APPLICATION NO. | : 10/185721 | |
| DATED | : April 25, 2006 | |
| INVENTOR(S) | : Bauer et al. | |

It is certified that error appears in the above-identified patent and that said Letters Patent is hereby corrected as shown below:

Column 10,
Line 20, "$C_1$ to $C_6$ acyloxy" should read --$C_1$ to $C_8$ acyloxy--.

Column 11,
Line 62, ""$C_1$ to $C_8$ acyloxy"" should read --$C_1$ to $C_8$ acyloxy--.

Signed and Sealed this

Twenty-first Day of November, 2006

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 476
<212> TYPE: PRT
<213> ORGANISM: Homo sapiens

<400> SEQUENCE: 1

Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
                20                  25                  30

Val Ala Gly Pro Leu Gly Gln Asn Leu Glu Val Glu Pro Tyr Ser Gln
            35                  40                  45

Tyr Ser Asn Val Gln Phe Pro Gln Val Gln Pro Gln Ile Ser Ser Ser
        50                  55                  60
```

```
Ser Tyr Tyr Ser Asn Leu Gly Phe Tyr Pro Gln Gln Pro Glu Glu Trp
 65                  70                  75                  80

Tyr Ser Pro Gly Ile Tyr Glu Leu Arg Arg Met Pro Ala Glu Thr Leu
                 85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
            115                 120                 125

Val Cys Gly Asp Arg Ala Ser Gly Tyr His Tyr Asn Ala Leu Thr Cys
130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Met Tyr Thr Gly Leu Leu Thr Glu Ile Gln Cys Lys
            195                 200                 205

Ser Lys Arg Leu Arg Lys Asn Val Lys Gln His Ala Asp Gln Thr Val
210                 215                 220

Asn Glu Asp Ser Glu Gly Arg Asp Leu Arg Gln Val Thr Ser Thr Thr
225                 230                 235                 240

Lys Ser Cys Arg Glu Lys Thr Glu Leu Thr Pro Asp Gln Gln Thr Leu
                245                 250                 255

Leu His Phe Ile Met Asp Ser Tyr Asn Lys Gln Arg Met Pro Gln Glu
            260                 265                 270

Ile Thr Asn Lys Ile Leu Lys Glu Glu Phe Ser Ala Glu Glu Asn Phe
            275                 280                 285

Leu Ile Leu Thr Glu Met Ala Thr Asn His Val Gln Val Leu Val Glu
290                 295                 300

Phe Thr Lys Lys Leu Pro Gly Phe Gln Thr Leu Asp His Glu Asp Gln
305                 310                 315                 320

Ile Ala Leu Leu Lys Gly Ser Ala Val Glu Ala Met Phe Leu Arg Ser
                325                 330                 335

Ala Glu Ile Phe Asn Lys Lys Leu Pro Ser Gly His Ser Asp Leu Leu
            340                 345                 350

Glu Glu Arg Ile Arg Asn Ser Gly Ile Ser Asp Glu Tyr Ile Thr Pro
            355                 360                 365

Met Phe Ser Phe Tyr Lys Ser Ile Gly Glu Leu Lys Met Thr Gln Glu
370                 375                 380

Glu Tyr Ala Leu Leu Thr Ala Ile Val Ile Leu Ser Pro Asp Arg Gln
385                 390                 395                 400

Tyr Ile Lys Asp Arg Glu Ala Val Glu Lys Leu Gln Glu Pro Leu Leu
                405                 410                 415

Asp Val Leu Gln Lys Leu Cys Lys Ile His Gln Pro Glu Asn Pro Gln
            420                 425                 430

His Phe Ala Cys Leu Leu Gly Arg Leu Thr Glu Leu Arg Thr Phe Asn
            435                 440                 445

His His His Ala Glu Met Leu Met Ser Trp Arg Val Asn Asp His Lys
450                 455                 460

Phe Thr Pro Leu Leu Cys Glu Ile Trp Asp Val Gln
465                 470                 475
```

<210> SEQ ID NO 2
<211> LENGTH: 1431
<212> TYPE: DNA
<213> ORGANISM: Homo sapiens

<400> SEQUENCE: 2

| | |
|---|---|
| atgggatcaa aaatgaatct cattgaacat tcccatttac ctaccacaga tgaattttct | 60 |
| ttttctgaaa atttatttgg tgttttaaca gaacaagtgg caggtcctct gggacagaac | 120 |
| ctggaagtgg aaccatactc gcaatacagc aatgttcagt tccccaagt tcaaccacag | 180 |
| atttcctcgt catcctatta ttccaacctg gtttctacc cccagcagcc tgaagagtgg | 240 |
| tactctcctg gaatatatga actcaggcgt atgccagctg agactctcta ccagggagaa | 300 |
| actgaggtag cagagatgcc tgtaacaaag aagccccgca tgggcgcgtc agcagggagg | 360 |
| atcaaagggg atgagctgtg tgttgtttgt ggagacagag cctctggata ccactataat | 420 |
| gcactgacct gtgagggtg taaaggtttc tcaggagaa gcattaccaa aaacgctgtg | 480 |
| tacaagtgta aaacgggggg caactgtgtg atggatatgt acatgcgaag aaagtgtcaa | 540 |
| gagtgtcgac taaggaaatg caaagagatg ggaatgttgg ctgaatgtat gtatacaggc | 600 |
| ttgttaactg aaattcagtg taaatctaag cgactgagaa aaaatgtgaa gcagcatgca | 660 |
| gatcagaccg tgaatgaaga cagtgaaggt cgtgacttgc gacaagtgac ctcgacaaca | 720 |
| aagtcatgca gggagaaaac tgaactcacc ccagatcaac agactcttct acattttatt | 780 |
| atggattcat ataacaaaca gaggatgcct caggaaataa caaataaaat tttaaaagaa | 840 |
| gaattcagtg cagaagaaaa ttttctcatt ttgacggaaa tggcaaccaa tcatgtacag | 900 |
| gttcttgtag aattcacaaa aaagctacca ggatttcaga cttttggacca tgaagaccag | 960 |
| attgctttgc tgaaagggtc tgcggttgaa gctatgttcc ttcgttcagc tgagattttc | 1020 |
| aataagaaac ttccgtctgg gcattctgac ctattggaag aaagaattcg aaatagtggt | 1080 |
| atctctgatg aatatataac acctatgttt agttttata aaagtattgg ggaactgaaa | 1140 |
| atgactcaag aggagtatgc tctgcttaca gcaattgtta tcctgtctcc agatagacaa | 1200 |
| tacataaagg atagagaggc agtagagaag cttcaggagc cacttcttga tgtgctacaa | 1260 |
| aagttgtgta agattcacca gcctgaaaat cctcaacact ttgcctgtct cctgggtcgc | 1320 |
| ctgactgaat tacggacatt caatcatcac acgctgaga tgctgatgtc atggagagta | 1380 |
| aacgaccaca gtttacccc acttctctgt gaaatctggg acgtgcagtg a | 1431 |

<210> SEQ ID NO 3
<211> LENGTH: 1263
<212> TYPE: PRT
<213> ORGANISM: Homo sapiens

<400> SEQUENCE: 3

Met Leu Val Lys Pro Leu Pro Asp Ser Glu Glu Glu Gly His Asp Asn
1               5                   10                  15

Gln Glu Ala His Gln Lys Tyr Glu Thr Met Gln Cys Phe Ala Val Ser
                20                  25                  30

Gln Pro Lys Ser Ile Lys Glu Glu Gly Glu Asp Leu Gln Ser Cys Leu
            35                  40                  45

Ile Cys Val Ala Arg Arg Val Pro Met Lys Glu Arg Pro Val Leu Pro
        50                  55                  60

Ser Ser Glu Ser Phe Thr Thr Arg Gln Asp Leu Gln Gly Lys Ile Thr
65                  70                  75                  80

Ser Leu Asp Thr Ser Thr Met Arg Ala Ala Met Lys Pro Gly Trp Glu

-continued

```
                    85                  90                  95
Asp Leu Val Arg Arg Cys Ile Gln Lys Phe His Ala Gln His Glu Gly
            100                 105                 110
Glu Ser Val Ser Tyr Ala Lys Arg His His Glu Val Leu Arg Gln
        115                 120                 125
Gly Leu Ala Phe Ser Gln Ile Tyr Arg Phe Ser Leu Ser Asp Gly Thr
        130                 135                 140
Leu Val Ala Ala Gln Thr Lys Ser Lys Leu Ile Arg Ser Gln Thr Thr
145                 150                 155                 160
Asn Glu Pro Gln Leu Val Ile Ser Leu His Met Leu His Arg Glu Gln
                165                 170                 175
Asn Val Cys Val Met Asn Pro Asp Leu Thr Gly Gln Thr Met Gly Lys
            180                 185                 190
Pro Leu Asn Pro Ile Ser Ser Asn Ser Pro Ala His Gln Ala Leu Cys
        195                 200                 205
Ser Gly Asn Pro Gly Gln Asp Met Thr Leu Ser Ser Asn Ile Asn Phe
        210                 215                 220
Pro Ile Asn Gly Pro Lys Glu Gln Met Gly Met Pro Met Gly Arg Phe
225                 230                 235                 240
Gly Gly Ser Gly Gly Met Asn His Val Ser Gly Met Gln Ala Thr Thr
                245                 250                 255
Pro Gln Gly Ser Asn Tyr Ala Leu Lys Met Asn Ser Pro Ser Gln Ser
            260                 265                 270
Ser Pro Gly Met Asn Pro Gly Gln Pro Thr Ser Met Leu Ser Pro Arg
        275                 280                 285
His Arg Met Ser Pro Gly Val Ala Gly Ser Pro Arg Ile Pro Pro Ser
        290                 295                 300
Gln Phe Ser Pro Ala Gly Ser Leu His Ser Pro Val Gly Val Cys Ser
305                 310                 315                 320
Ser Thr Gly Asn Ser His Ser Tyr Thr Asn Ser Ser Leu Asn Ala Leu
                325                 330                 335
Gln Ala Leu Ser Glu Gly His Gly Val Ser Leu Gly Ser Ser Leu Ala
            340                 345                 350
Ser Pro Asp Leu Lys Met Gly Asn Leu Gln Asn Ser Pro Val Asn Met
        355                 360                 365
Asn Pro Pro Leu Ser Lys Met Gly Ser Leu Asp Ser Lys Asp Cys
        370                 375                 380
Phe Gly Leu Tyr Gly Glu Pro Ser Glu Gly Thr Thr Gly Gln Ala Glu
385                 390                 395                 400
Ser Ser Cys His Pro Gly Glu Gln Lys Glu Thr Asn Asp Pro Asn Leu
                405                 410                 415
Pro Pro Ala Val Ser Ser Glu Arg Ala Asp Gly Gln Ser Arg Leu His
            420                 425                 430
Asp Ser Lys Gly Gln Thr Lys Leu Leu Gln Leu Leu Thr Thr Lys Ser
        435                 440                 445
Asp Gln Met Glu Pro Ser Pro Leu Ala Ser Ser Leu Ser Asp Thr Asn
        450                 455                 460
Lys Asp Ser Thr Gly Ser Leu Pro Gly Ser Gly Ser Thr His Gly Thr
465                 470                 475                 480
Ser Leu Lys Glu Lys His Lys Ile Leu His Arg Leu Leu Gln Asp Ser
                485                 490                 495
Ser Ser Pro Val Asp Leu Ala Lys Leu Thr Ala Glu Ala Thr Gly Lys
            500                 505                 510
```

-continued

```
Asp Leu Ser Gln Glu Ser Ser Thr Ala Pro Gly Ser Glu Val Thr
        515                 520                 525
Ile Lys Gln Glu Pro Val Ser Pro Lys Lys Glu Asn Ala Leu Leu
    530                 535                 540
Arg Tyr Leu Leu Asp Lys Asp Thr Lys Asp Ile Gly Leu Pro Glu
545                 550                 555                 560
Ile Thr Pro Lys Leu Glu Arg Leu Asp Ser Lys Thr Asp Pro Ala Ser
            565                 570                 575
Asn Thr Lys Leu Ile Ala Met Lys Thr Glu Lys Glu Met Ser Phe
        580                 585                 590
Glu Pro Gly Asp Gln Pro Gly Ser Glu Leu Asp Asn Leu Glu Glu Ile
        595                 600                 605
Leu Asp Asp Leu Gln Asn Ser Gln Leu Pro Gln Leu Phe Pro Asp Thr
        610                 615                 620
Arg Pro Gly Ala Pro Ala Gly Ser Val Asp Lys Gln Ala Ile Ile Asn
625                 630                 635                 640
Asp Leu Met Gln Leu Thr Ala Glu Asn Ser Pro Val Thr Pro Val Gly
            645                 650                 655
Ala Gln Lys Thr Ala Leu Arg Ile Ser Gln Ser Thr Phe Asn Asn Pro
        660                 665                 670
Arg Pro Gly Gln Leu Gly Arg Leu Leu Pro Asn Gln Asn Leu Pro Leu
        675                 680                 685
Asp Ile Thr Leu Gln Ser Pro Thr Gly Ala Gly Pro Phe Pro Pro Ile
        690                 695                 700
Arg Asn Ser Ser Pro Tyr Ser Val Ile Pro Gln Pro Gly Met Met Gly
705                 710                 715                 720
Asn Gln Gly Met Ile Gly Asn Gln Gly Asn Leu Gly Asn Ser Ser Thr
            725                 730                 735
Gly Met Ile Gly Asn Ser Ala Ser Arg Pro Thr Met Pro Ser Gly Glu
        740                 745                 750
Trp Ala Pro Gln Ser Ser Ala Val Arg Val Thr Cys Ala Ala Thr Thr
        755                 760                 765
Ser Ala Met Asn Arg Pro Val Gln Gly Gly Met Ile Arg Asn Pro Ala
        770                 775                 780
Ala Ser Ile Pro Met Arg Pro Ser Ser Gln Pro Gly Gln Arg Gln Thr
785                 790                 795                 800
Leu Gln Ser Gln Val Met Asn Ile Gly Pro Ser Glu Leu Glu Met Asn
            805                 810                 815
Met Gly Gly Pro Gln Tyr Ser Gln Gln Gln Ala Pro Pro Asn Gln Thr
        820                 825                 830
Ala Pro Trp Pro Glu Ser Ile Leu Pro Ile Asp Gln Ala Ser Phe Ala
        835                 840                 845
Ser Gln Asn Arg Gln Pro Phe Gly Ser Ser Pro Asp Asp Leu Leu Cys
        850                 855                 860
Pro His Pro Ala Ala Glu Ser Pro Ser Asp Glu Gly Ala Leu Leu Asp
865                 870                 875                 880
Gln Leu Tyr Leu Ala Leu Arg Asn Phe Asp Gly Leu Glu Glu Ile Asp
            885                 890                 895
Arg Ala Leu Gly Ile Pro Glu Leu Val Ser Gln Ser Gln Ala Val Asp
        900                 905                 910
Pro Glu Gln Phe Ser Ser Gln Asp Ser Asn Ile Met Leu Glu Gln Lys
        915                 920                 925
```

```
Ala Pro Val Phe Pro Gln Gln Tyr Ala Ser Gln Ala Gln Met Ala Gln
    930                 935                 940
Gly Ser Tyr Ser Pro Met Gln Asp Pro Asn Phe His Thr Met Gly Gln
945                 950                 955                 960
Arg Pro Ser Tyr Ala Thr Leu Arg Met Gln Pro Arg Pro Gly Leu Arg
                965                 970                 975
Pro Thr Gly Leu Val Gln Asn Gln Pro Asn Gln Leu Arg Leu Gln Leu
            980                 985                 990
Gln His Arg Leu Gln Ala Gln Asn Arg Gln Pro Leu Met Asn Gln
        995                 1000                1005
Ile Ser Asn Val Ser Asn Val Asn Leu Thr Leu Arg Pro Gly Val Pro
   1010                 1015                1020
Thr Gln Ala Pro Ile Asn Ala Gln Met Leu Ala Gln Arg Gln Arg Glu
1025                1030                1035                1040
Ile Leu Asn Gln His Leu Arg Gln Arg Gln Met His Gln Gln Gln
                1045                1050                1055
Val Gln Gln Arg Thr Leu Met Met Arg Gly Gln Gly Leu Asn Met Thr
            1060                1065                1070
Pro Ser Met Val Ala Pro Ser Gly Met Pro Ala Thr Met Ser Asn Pro
   1075                 1080                1085
Arg Ile Pro Gln Ala Asn Ala Gln Gln Phe Pro Phe Pro Pro Asn Tyr
   1090                 1095                1100
Gly Ile Ser Gln Gln Pro Asp Pro Gly Phe Thr Gly Ala Thr Thr Pro
1105                1110                1115                1120
Gln Ser Pro Leu Met Ser Pro Arg Met Ala His Thr Gln Ser Pro Met
                1125                1130                1135
Met Gln Gln Ser Gln Ala Asn Pro Ala Tyr Gln Ala Pro Ser Asp Ile
            1140                1145                1150
Asn Gly Trp Ala Gln Gly Asn Met Gly Gly Asn Ser Met Phe Ser Gln
        1155                1160                1165
Gln Ser Pro Pro His Phe Gly Gln Gln Ala Asn Thr Ser Met Tyr Ser
   1170                 1175                1180
Asn Asn Met Asn Ile Asn Val Ser Met Ala Thr Asn Thr Gly Gly Met
1185                1190                1195                1200
Ser Ser Met Asn Gln Met Thr Gly Gln Ile Ser Met Thr Ser Val Thr
                1205                1210                1215
Ser Val Pro Thr Ser Gly Leu Ser Ser Met Gly Pro Glu Gln Val Asn
            1220                1225                1230
Asp Pro Ala Leu Arg Gly Gly Asn Leu Phe Pro Asn Gln Leu Pro Gly
        1235                1240                1245
Met Asp Met Ile Lys Gln Glu Gly Asp Thr Thr Arg Lys Tyr Cys
   1250                 1255                1260

<210> SEQ ID NO 4
<211> LENGTH: 6158
<212> TYPE: DNA
<213> ORGANISM: Homo sapiens

<400> SEQUENCE: 4
ggcggccgca gcctcggcta cagcttcggc ggcgaaggtc agcgccgacg gcagccggca        60
cctgacggcg tgaccgaccc gagccgattt ctcttggatt tggctacaca cttatagatc       120
ttctgcactg tttacaggca cagttgctga tatgtgttca agatgagtgg gatgggagaa       180
aatacctctg acccctccag ggcagagaca agaaagcgca ggaatgtcc tgaccaactt        240
```

-continued

| | |
|---|---|
| ggacccagcc ccaaaaggaa cactgaaaaa cgtaatcgtg aacaggaaaaa taaatatata | 300 |
| gaagaacttg cagagttgat tttttgcaaat tttaatgata tagacaactt taacttcaaa | 360 |
| cctgacaaat gtgcaatctt aaaagaaact gtgaagcaaa ttcgtcagat caaagaacaa | 420 |
| gagaaagcag cagctgccaa catagatgaa gtgcagaagt cagatgtatc ctctacaggg | 480 |
| cagggtgtca tcgacaagga tgcgctgggg cctatgatgc ttgaggccct tgatgggttc | 540 |
| ttctttgtag tgaacctgga aggcaacgtt gtgtttgtgt cagagaatgt gacacagtat | 600 |
| ctaaggtata accaagaaga gctgatgaac aaaagtgtat atagcatctt gcatgttggg | 660 |
| gaccacacgg aatttgtcaa aaacctgctg ccaaagtcta taggtaaatg ggggatcttg | 720 |
| gtctggcgaa cctccgaggc ggaacagcca taccttcaat tgtcggatgc tggtaaaacc | 780 |
| tttacctgat tcagaagagg agggtcatga taaccaggaa gctcatcaga aatatgaaac | 840 |
| tatgcagtgc ttcgctgtct ctcaaccaaa gtccatcaaa aagaaggag aagatttgca | 900 |
| gtcctgcttg atttgcgtgg caagaagagt tcccatgaag aaagaccag ttcttccctc | 960 |
| atcagaaagt tttactactc gccaggatct ccaaggcaag atcacgtctc tggataccag | 1020 |
| caccatgaga gcagccatga aaccaggctg gaggacctg gtaagaaggt gtattcagaa | 1080 |
| gttccatgcg cagcatgaag gagaatctgt gtcctatgct aagaggcatc atcatgaagt | 1140 |
| actgagacaa ggattggcat tcagtcaaat ctatcgtttt tccttgtctg atggcactct | 1200 |
| tgttgctgca caaacgaaga gcaaactcat ccgttctcag actactaatg aacctcaact | 1260 |
| tgtaatatct ttacatatgc ttcacagaga gcagaatgtg tgtgtgatga atccggatct | 1320 |
| gactggacaa acgatgggga agccactgaa tccaattagc tctaacagcc ctgcccatca | 1380 |
| ggccctgtgc agtgggaacc caggtcagga catgaccctc agtagcaata taaattttcc | 1440 |
| cataaatggc ccaaaggaac aaatgggcat gcccatgggc aggtttggtg ttctggggg | 1500 |
| aatgaaccat gtgtcaggca tgcaagcaac cactcctcag ggtagtaact atgcactcaa | 1560 |
| aatgaacagc ccctcacaaa gcagccctgg catgaatcca ggacagccca cctccatgct | 1620 |
| ttcaccaagg catcgcatga gccctggagt ggctggcagc cctcgaatcc cacccagtca | 1680 |
| gttttccccct gcaggaagct tgcattcccc tgtgggagtt tgcagcagca caggaaatag | 1740 |
| ccatagttat accaacagct ccctcaatgc acttcaggcc ctcagcgagg ggcacggggt | 1800 |
| ctcattaggg tcatcgttgg cttcaccaga cctaaaaatg ggcaatttgc aaaactcccc | 1860 |
| agttaatatg aatcctcccc cactcagcaa gatgggaagc ttggactcaa aagactgttt | 1920 |
| tggactatat ggggagccct ctgaaggtac aactggacaa gcagagagca gctgccatcc | 1980 |
| tggagagcaa aaggaaacaa atgaccccaa cctgccccccg gccgtgagca gtgagagagc | 2040 |
| tgacgggcag agcagactgc atgacagcaa aagggcagacc aaaactcctgc agctgctgac | 2100 |
| caccaaatct gatcagatgg agccctcgcc cttagccagc tctttgtcgg atacaaacaa | 2160 |
| agactccaca ggtagcttgc ctggttctgg gtctacacat ggaacctcgc tcaaggagaa | 2220 |
| gcataaaatt ttgcacagac tcttgcagga cagcagttcc cctgtggact tggccaagtt | 2280 |
| aacagcagaa gccacaggca aagacctgag ccaggagtcc agcagcacag ctcctggatc | 2340 |
| agaagtgact attaaacaag agccggtgag ccccaagaag aaagagaatg cactacttcg | 2400 |
| ctatttgcta gataaagatg atactaaaga tattggttta ccagaaataa cccccaaact | 2460 |
| tgagagactg gacagtaaga cagatcctgc cagtaacaca aaattaatag caatgaaaac | 2520 |
| tgagaaggag gagatgagct ttgagcctgg tgaccagcct ggcagtgagc tggacaactt | 2580 |
| ggaggagatt ttggatgatt tgcagaatag tcaattacca cagcttttcc cagacacgag | 2640 |

-continued

```
gccaggcgcc cctgctggat cagttgacaa gcaagccatc atcaatgacc tcatgcaact    2700
cacagctgaa aacagccctg tcacacctgt tggagcccag aaaacagcac tgcgaatttc    2760
acagagcact tttaataacc cacgaccagg caactgggc aggttattgc caaaccagaa     2820
tttaccactt gacatcacat tgcaaagccc aactggtgct ggacctttcc caccaatcag    2880
aaacagtagt ccctactcag tgatacctca gccaggaatg atgggtaatc aagggatgat    2940
aggaaaccaa ggaaatttag ggaacagtag cacaggaatg attggtaaca gtgcttctcg    3000
gcctactatg ccatctggag aatgggcacc gcagagttcg gctgtgagag tcacctgtgc    3060
tgctaccacc agtgccatga accggccagt ccaaggaggt atgattcgga acccagcagc    3120
cagcatcccc atgaggccca gcagccagcc tggccaaaga cagacgcttc agtctcaggt    3180
catgaatata gggccatctg aattagagat gaacatgggg ggacctcagt atagccaaca    3240
acaagctcct ccaaatcaga ctgccccatg gcctgaaagc atcctgccta tagaccaggc    3300
gtcttttgcc agccaaaaca ggcagccatt tggcagttct ccagatgact tgctatgtcc    3360
acatcctgca gctgagtctc cgagtgatga gggagctctc ctggaccagc tgtatctggc    3420
cttgcggaat tttgatggcc tggaggagat tgatagagcc ttaggaatac ccgaactggt    3480
cagccagagc caagcagtag atccagaaca gttctcaagt caggattcca acatcatgct    3540
ggagcagaag gcgcccgttt cccacagca gtatgcatct caggcacaaa tggcccaggg    3600
tagctattct cccatgcaag atccaaactt tcacaccatg ggacagcggc ctagttatgc    3660
cacactccgt atgcagccca gaccgggcct caggcccacg ggcctagtgc agaaccagcc    3720
aaatcaacta agacttcaac ttcagcatcg cctccaagca cagcagaatc gccagccact    3780
tatgaatcaa atcagcaatg tttccaatgt gaacttgact ctgaggcctg gagtaccaac    3840
acaggcacct attaatgcac agatgctggc ccagagacag agggaaatcc tgaaccagca    3900
tcttcgacag agacaaatgc atcagcaaca gcaagttcag caacgaactt tgatgatgag    3960
aggacaaggg ttgaatatga caccaagcat ggtggctcct agtggtatgc cagcaactat    4020
gagcaaccct cggattcccc aggcaaatgc acagcagttt ccatttcctc caaactacgg    4080
aataagtcag caacctgatc caggctttac tggggctacg actccccaga gcccacttat    4140
gtcaccccga atggcacata cacagagtcc catgatgcaa cagtctcagg ccaacccagc    4200
ctatcaggcc ccctccgaca taaatggatg ggcgcagggg aacatgggcg gaaacagcat    4260
gttttcccag cagtccccac cacactttgg gcagcaagca acaccagca tgtacagtaa    4320 caacatgaac atcaatgtgt ccatggcgac caacacaggt ggcatgagca gcatgaacca    4380
gatgacagga cagatcagca tgacctcagt gacctccgtg cctacgtcag gctgtcctc    4440 catgggtccc gagcaggtta atgatcctgc tctgaggga ggcaacctgt tcccaaacca    4500
gctgcctgga atggatatga ttaagcagga gggagacaca acacggaaat attgctgaca    4560
ctgctgaagc cagttgcttc ttcagctgac cgggctcact tgctcaaaac acttccagtc    4620
tggagagctg tgtctatttg tttcaaccca actgacctgc cagccggttc tgctagagca    4680
gacaggcctg gccctggttc ccagggtggc gtccactcgg ctgtggcagg aggagctgcc    4740
tcttctcttg acagtctgaa gctcgcatcc agacagtcgc tcagtctgtt cactgcattc    4800
accttagtgc aacttagatc tctcctgcaa agtaaatgt tgcaggcaa atttcatacc    4860 catgtcagat tgaatgtatt taaatgtatg tatttaagga gaaccatgct cttgttctgt    4920
```

```
tcctgttcgg ttccagacac tggtttcttg ctttgttttc cctggctaac agtctagtgc      4980
aaaagattaa gattttatct gggggaaaga aaagaatttt ttaaaaaatt aaactaaaga      5040
tgttttaagc taaagcctga atttgggatg gaagcaggac agacaccgtg gacagcgctg      5100
tatttacaga cacacccagt gcgtgaagac caacaaagtc acagtcgtat ctctagaaag      5160
ctctaaagac catgttggaa agagtctcca gttactgaac agatgaaaag gagcctgtga      5220
gagggctgtt aacattagca aatattttt ccttgttttt tctttgttaa aaccaaactg       5280
gttcacctga atcatgaatt gagaagaaat aattttcatt tctaaattaa gtccctttta     5340
gtttgatcag acagcttgaa tcagcatctc ttcttccctg tcagcctgac tcttcccttc     5400
ccctctctca ttccccatac tccctatttt cattccttt ttaaaaaata atataagcta      5460
cagaaaccag gtaagccctt tatttcctta aatgttttgc cagccactta ccaattgcta     5520
agtattgaat ttcagaaaaa aaaaatgcat ttactggcaa ggagaagagc aaagttaagg     5580
cttgatacca atcgagctaa ggatacctgc tttggaagca tgtttattct gttccccagc     5640
aactctggcc tccaaaatgg gagaaaacgc cagtgtgttt aaattgatag cagatatcac     5700
gacagattta acctctgcca tgtgtttttt attttgtttt ttagcagtgc tgactaagcc     5760
gaagttttgt aaggtacata aaatccaatt tatatgtaaa caagcaataa tttaagttga    5820
gaacttatgt gttttaattg tataattttt gtgaggtata catattgtgg aattgactca    5880
aaaatgaggt acttcagtat taaattagat atcttcatag caatgtctcc taaaggtgtt    5940
ttgtaaagga tatcaatgcc ttgattagac ctaatttgta gacttaagac ttttttatttt   6000 ctaaaccttg tgattctgct tataagtcat ttatctaatc tatatgatat gcagccgctg    6060
taggaaccaa ttcttgattt ttatatgttt atattctttc ttaatgaacc ttagaaagac   6120
tacatgttac taagcaggcc acttttatgg ttgtttt                              6158
```

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 5
cccagggtga ataacctcgg ggctctgtcc ctccaatccc agggtgaata acctcggg        58